(12) United States Patent
Matsuo et al.

(10) Patent No.: US 11,453,761 B2
(45) Date of Patent: Sep. 27, 2022

(54) COMPOSITE MATERIAL, CURABLE COMPOSITION, AND METHOD FOR PRODUCING CURABLE COMPOSITION

(71) Applicant: TOKUYAMA DENTAL CORPORATION, Tokyo (JP)

(72) Inventors: Takuma Matsuo, Tokyo (JP); Hiroshi Morisaki, Tokyo (JP); Hironobu Akizumi, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 55 days.

(21) Appl. No.: 17/273,225

(22) PCT Filed: Aug. 29, 2019

(86) PCT No.: PCT/JP2019/033882
§ 371 (c)(1),
(2) Date: Mar. 3, 2021

(87) PCT Pub. No.: WO2020/050123
PCT Pub. Date: Mar. 12, 2020

(65) Prior Publication Data
US 2021/0324178 A1   Oct. 21, 2021

(30) Foreign Application Priority Data

Sep. 5, 2018 (JP) .............................. JP2018-165680
Dec. 4, 2018 (JP) .............................. JP2018-227112

(51) Int. Cl.
*C08K 7/18* (2006.01)
*A61K 6/887* (2020.01)
(Continued)

(52) U.S. Cl.
CPC ................. *C08K 7/18* (2013.01); *A61K 6/16* (2020.01); *A61K 6/17* (2020.01); *A61K 6/76* (2020.01);
(Continued)

(58) Field of Classification Search
CPC combination set(s) only.
See application file for complete search history.

(56) References Cited

U.S. PATENT DOCUMENTS 5,057,018 A * 10/1991 Bowen ................... A61K 6/822
106/35
6,699,559 B1 * 3/2004 Milburn ................ F24S 80/525
359/359

(Continued)

FOREIGN PATENT DOCUMENTS

CN    108289795 A    7/2018
JP    H09255516 A    9/1997
(Continued)

OTHER PUBLICATIONS

International Search Report issued in International Application No. PCT/JP2019/033882, dated Nov. 5, 2019 (2 pages).

(Continued)

*Primary Examiner* — Peter A Salamon
(74) *Attorney, Agent, or Firm* — Osha Bergman Watanabe & Burton LLP

(57) ABSTRACT

Provided is a composite material which comprises a resin matrix and inorganic particles dispersed therein, wherein the inorganic particles comprise: one or more groups (G-PID) of spherical particles uniform in particle diameter which comprise aggregates of inorganic spherical particles having a specific average primary-particle diameter, have a narrow particle-size-distribution width, and have a lower refractive index than the resin matrix; and a group (G-SFP) of ultrafine particles. The inorganic spherical particles which constitute all the groups of spherical particles uniform in particle diameter contained in the resin matrix have an arrangement structure which is a short-range order structure satisfying a specific requirement. Also provided are a curable composition giving the composite material and a method for producing the curable composition.

11 Claims, 5 Drawing Sheets

(51) Int. Cl.

| | |
|---|---|
| *A61K 6/831* | (2020.01) |
| *A61K 6/76* | (2020.01) |
| *A61K 6/16* | (2020.01) |
| *A61K 6/17* | (2020.01) |
| *C08F 222/10* | (2006.01) |
| *C08F 2/44* | (2006.01) |
| *C08F 2/50* | (2006.01) |
| *C08K 3/36* | (2006.01) |

(52) U.S. Cl.
CPC .............. *A61K 6/831* (2020.01); *A61K 6/887* (2020.01); *C08F 2/44* (2013.01); *C08F 2/50* (2013.01); *C08F 222/102* (2020.02); *C08K 3/36* (2013.01); *C08K 2201/003* (2013.01); *C08K 2201/011* (2013.01)

(56) References Cited

U.S. PATENT DOCUMENTS

| | | | | |
|---|---|---|---|---|
| 2014/0141255 | A1* | 5/2014 | Kano | C23C 16/45525 428/473.5 |
| 2015/0272833 | A1* | 10/2015 | Toriyabe | A61K 6/61 522/48 |
| 2017/0049665 | A1* | 2/2017 | Kita | A61K 6/831 |
| 2018/0303721 | A1 | 10/2018 | Akizumi et al. | |
| 2019/0292278 | A1* | 9/2019 | Akizumi | A61K 6/76 |
| 2021/0324178 | A1* | 10/2021 | Matsuo | A61K 6/887 |

FOREIGN PATENT DOCUMENTS

| | | | |
|---|---|---|---|
| JP | 2008260720 A | 10/2008 | |
| JP | 2010058091 A | 3/2010 | |
| JP | 2012153640 A | 8/2012 | |
| JP | 5274164 B2 | 8/2013 | |
| WO | 2014050634 A1 | 4/2014 | |
| WO | 2015125470 A1 | 8/2015 | |
| WO | 2017069274 A1 | 4/2017 | |
| WO | 2018101236 A1 | 6/2018 | |
| WO | WO-2018101236 A1 * | 6/2018 | .............. A61K 6/08 |

OTHER PUBLICATIONS

Written Opinion issued in International Application No. PCT/JP2019/033882, dated Nov. 5, 2019 (3 pages).

T. Knarvang, "Mixing of experimental composites," NIOM Newsletter, XP055905279, Oslo, Norway: Retrieved from the Internet: URL:https://niom.no/mixing-of-experimental-composites/ <https://protect-us.mimecast.com/s/vRwXCpY7LMUVyrmUPjOuz?domain=niom.no/> [retrieved on Mar. 25, 2022], Jan. 29, 2014 (2 pages).

Extended European Search Report issued in corresponding European Application No. 19856804.0; dated Apr. 5, 2022 (10 pages).

\* cited by examiner

RADIAL DISTRIBUTION FUNCTION

RADIAL DISTRIBUTION FUNCTION

RADIAL DISTRIBUTION FUNCTION

RADIAL DISTRIBUTION FUNCTION

RADIAL DISTRIBUTION FUNCTION

COMPOSITE MATERIAL, CURABLE COMPOSITION, AND METHOD FOR PRODUCING CURABLE COMPOSITION

CROSS-REFERENCE TO RELATED APPLICATIONS

This application is a U.S. national phase application based on the PCT Application No. PCT/JP2019/033882 filed on Aug. 29, 2019, which claims a priority to and benefits of Japanese Application No. 2018-165680, filed on Sep. 5, 2018 and Japanese Application No. 2018-227112, filed on Dec. 4, 2018, the entire contents of which are incorporated herein by reference.

TECHNICAL FIELD

The present invention relates to a composite material in which inorganic particles are dispersed in a resin matrix, a curable composition which provides the composite material, and a method for producing the curable composition. More specifically, the present invention relates to a composite material in which an appearance color tone can be controlled without use of a dye, a pigment or the like, in which fading and discoloration are unlikely to occur, which can be restored so as to be excellent in convenience and aesthetic property, and which is suitably used as a dental filling restorative material; a curable composition which provides the composite material; and a method for producing the curable composition.

BACKGROUND ART

A dental composite resin (hereinafter also referred to as the "CR") is one type of material for restoring teeth which are damaged by dental caries, fractures, and the like, and is formed of a curable composition which contains a polymerizable monomer and an inorganic filler. Restoration (CR restoration) using the dental composite resin (CR) has rapidly come into widespread use; for example, because the amount of tooth substance which is cut can be reduced, a color tone equivalent to natural teeth can be provided and the operation thereof is easily performed. In recent years, as a result of the enhancement of a mechanical strength and the enhancement of an adhesive force to teeth, the dental composite resin has been used not only for the restoration of anterior teeth, but also for molar teeth to which a high occlusal pressure is applied.

Although as described above, one of the excellent characteristics of the CR restoration is that highly aesthetic restoration can be performed, in order to perform highly aesthetic restoration, it is necessary to determine the color (hue and color tone) of the teeth (restored teeth) which are restored (this type of color determination may be referred to as "shade taking") and to select a CR whose color is compatible with the determined color so as to perform restoration. Although in this case, one color of CR may be used to perform restoration, when highly aesthetic restoration is performed so as to faithfully reproduce color changes in parts of the teeth, a plurality of CRs having different colors may be stacked in layers so as to perform restoration.

In the CR restoration including the aesthetic restoration as described above, one or a plurality of types of CRs, whose color tones are adjusted by changing the types and the amounts of pigment substances or dye substances which are mixed and then added, are generally used. However, in the CR in which pigment substances or dye substances are used to adjust the color tones, these substances in the cured product of the CR deteriorate with time so as to be subjected to fading or discoloration, and thus as time passes after the restoration, discoloration occurs, with the result that the appearance of a restored part may be prevented from being compatible with natural teeth.

On the other hand, as a technology in which coloring is performed without use of pigment substances or dye substances, there is a technology in which color production is performed by utilization of the reflection, interference, scattering, transmission, and the like of light caused by fine particles in a medium, and a technology is also known in which the technology described above is applied to produce the desired color of a composite material where inorganic particles are dispersed in a medium such as a resin (see, for example, Patent Documents 1 and 2).

For example, Patent Document 1 discloses that in "a fine particle-dispersed product where first fine particles whose average particle diameter is in a range of 50 nm to 1 μm and whose Cv value of a particle diameter is equal to or less than 10% are dispersed in a medium, where the arrangement structure of the first fine particles in the dispersed product is an amorphous structure and where a short-range order structure which satisfies a specific condition defined by a "radial distribution function g(r) within a plane" is provided", the arrangement structure of the fine particles is stably maintained, light of a specific wavelength can be reflected, and the angle dependence of the reflected light in which the peak wavelength of the reflected light changes with a change in the incident angle of the light can be sufficiently reduced.

Patent Document 2 discloses "a curable composition which includes a polymerizable monomer component (A), a spherical filler (B) whose average particle diameter is within a range of 230 to 1000 nm and a polymerization initiator (C), in which 90% or more of individual particles of the spherical filler (B) are present within a range of plus or minus 5% of the average particle diameter and which satisfies a condition where the refractive index $n_F$ of the spherical filler (B) at 25° C. is higher than the refractive index $n_P$ of a polymer obtained by polymerizing the polymerizable monomer component (A) at 25° C.", and in "the curable composition, each individual value (V) of a colorimetric value which is measured, in a state where a cured product having a thickness of 1 mm is formed, with a color difference meter, in the Munsell color system of colored light under a black background is less than 5 and the chroma (C) thereof is equal to or greater than 0.05, and the value (V) of a colorimetric value in the Munsell color system of colored light under a white background is equal to or greater than 6 and the chroma (C) thereof is less than 2". Patent Document 2 then discloses that a CR formed of the curable composition described above has excellent characteristics in which (1) since dye substances or pigment substances are not used, the problem of chronological discoloration is unlikely to occur, in which (2) the cured product thereof can be colored yellow to red, which are the same colors as dentin colors (according to the average particle diameter of the spherical filler used), and in which moreover, (3) since the cured product has moderate transparency, the colors are easily harmonized with the colors of restored teeth, and without complicated shade taking and shade selection of the composite resin being performed, with one type of CR, the appearance of the restored teeth having a wide range of colors can be restored close to the appearance of natural teeth.

Patent Document 2 also discloses that when the average particle diameter of the spherical filler used is less than 100 nm, the development of a structural color is unlikely to occur, and that when the spherical filler having an average particle diameter equal to or greater than 150 nm and less than 230 nm is used, a bluish structural color is developed, and thus it is unlikely that the bluish structural color is harmonized with the color tone of the dentin surface of a restoration cavity deep portion.

Patent Document 1: Japanese Patent No. 5274164
Patent Document 2: PCT International Publication No. WO2017/069274

DISCLOSURE OF THE INVENTION

Problems to be Solved by the Invention

It is found from Patent Document 1 that the fine particles having a uniform particle diameter are dispersed so as to achieve an amorphous structure as a whole while having a specific short-range order structure, and that thus a structural color of a constant color tone can be produced without being affected by a change in the incident angle of light. In the description of Patent Document 2, colored light caused by interference of the cured product of the curable composition (or a CR formed of the curable composition) is produced in a portion in which the particles thereof are accumulated relatively regularly, and colored light caused by scattering is produced in a portion in which the particles thereof are dispersed randomly, and thus it can be inferred that even in this system, a balance between long-distance irregularity and short-distance regularity in the dispersed state of the spherical filler is important in order to obtain the effects described above.

However, in the CR disclosed in Patent Document 2, the balance for obtaining the effects described above is not quantitatively evaluated, and thus it is not clear what influences are exerted on the effects described above, for example, when a fine filler is added in order to adjust the viscosity of the CR and to adjust the contrast ratio of the cured product. In Patent Document 2, as the spherical filler (B), only one type of "aggregate which is formed with inorganic spherical particles having a predetermined average primary particle diameter within a range of 230 to 1000 nm and in which in a number-based particle size distribution of the aggregate, 90% or more of all particles are present within a range of plus or minus 5% of the predetermined average particle diameter" is used, and thus it is not clear what influences are exerted on the effects described above when a plurality of aggregates having different average primary particle diameters are used. Furthermore, it is found that depending on conditions under which individual components are kneaded so as to prepare the CR, even at an extremely low frequency, desired effects are not obtained.

Hence, an object of the present invention is to provide a composite material which can achieve the effects described above even when in a composite material like the cured product of the curable composition disclosed in Patent Document 2, a fine filler or a plurality of spherical filler aggregates for adjusting the viscosity of the curable composition or for adjusting the contrast ratio of the cured product are used, a curable composition which provides the composite material and a method for producing the curable composition.

Means for Solving the Problems

The present inventors have performed thorough studies on a case where as a method of quantifying the dispersed state of spherical particles, a method of defining the short-range order structure with the "radial distribution function g(r) within a plane" that is disclosed in Patent Document 1 is utilized, and where a fine filler or a plurality of spherical filler aggregates for adjusting the viscosity of a curable composition or for adjusting the contrast ratio of a cured product are used. Consequently, the present inventors have succeeded in identifying a short-range order structure with which effects are obtained in the system as disclosed in Patent Document 2, have confirmed that even when an superfine inorganic filler is added, the effect of developing a structural color is little affected and that when a specific condition is satisfied, even if a plurality of spherical filler aggregates are used, a short-range order structure type which produces a structural color in each of the spherical filler aggregates is kept, the structural color caused by each of the aggregates is produced and color production is performed with a color tone obtained by combining them as a whole and thereby have completed the present invention.

Specifically, a first aspect of the present invention is a composite material that includes a resin matrix and inorganic particles dispersed in a resin matrix, the inorganic particles including:

an identical particle diameter spherical particle group (G-PID) which is formed with an aggregate of inorganic spherical particles having a predetermined average primary particle diameter within a range of 100 to 1000 nm and in which in the number-based particle size distribution of the aggregate, 90% or more of all the particles are present within a range of plus or minus 5% of the predetermined average primary particle diameter; and a superfine particle group (G-SFP) that is formed with inorganic particles whose average primary particle diameter is less than 100 nm, the number of the identical particle diameter spherical particle groups included in the inorganic particles is one or more, when the number of the identical particle diameter spherical particle groups included in the inorganic particles is assumed to be a, and each of the identical particle diameter spherical particle groups are represented as $G\text{-}PID_m$ (where when a is 1, m is 1 whereas when a is equal to or greater than 2, m is a natural number from 1 to a) respectively in ascending order of the average primary particle diameters thereof, the average primary particle diameters of each $G\text{-}PID_m$ differ from each other by 25 nm or more, the average primary particle diameter of the superfine particle group is smaller than the average primary particle diameter of $G\text{-}PID_1$ by 25 nm or more, when the refractive index of the resin matrix at 25° C. is assumed to be $n_{(MX)}$, and the refractive index of the inorganic spherical particles of each $G\text{-}PID_m$ at 25° C. is assumed to be $n_{(G\text{-}PIDm)}$, for any $n_{(G\text{-}PIDm)}$, a relationship of $n_{(MX)} < n_{(G\text{-}PIDm)}$ holds true and an arrangement structure of the inorganic spherical particles of all the identical particle diameter spherical particle groups in the resin matrix is a composite material having a short-range order structure which satisfies conditions 1 and 2 below:

[Condition 1] when a dimensionless number $(r/r_0)$ which is standardized by dividing a distance r from the center of an arbitrary one of the inorganic spherical particles dispersed in the composite material by the average particle diameter $r_0$ of all the inorganic spherical particles dispersed in the composite material is assumed to be an x-axis, and a radial distribution function g(r) indicating a probability that another inorganic spherical particle is present at a point the distance r away from the center of the arbitrary inorganic spherical particle is assumed to be a y-axis, in a radial distribution function graph indicating a relationship of $r/r_0$ and g(r) which corresponds to r at that time, a closest particle-to-particle distance $r_1$ which is defined as r corresponding to the peak top of a peak closest to an origin among peaks appearing in the radial distribution function graph is a value that is 1 to 2 times the average particle diameter $r_0$ of all the inorganic spherical particles dispersed in the composite material;

[Condition 2] when r corresponding to the peak top of a peak second closest to the origin among the peaks appearing in the radial distribution function graph is assumed to be a second closest particle-to-particle distance $r_2$, a local minimum value of the radial distribution function g(r) between the closest particle-to-particle distance $r_1$ and the second closest particle-to-particle distance $r_2$ is a value of 0.56 to 1.10.

Preferably, in the composite material described above, based on the average particle density $<\rho>$ of the inorganic spherical particles within an observation plane, the number do of inorganic spherical particles which are present in a region between a circle of a distance r from an arbitrary inorganic spherical particle within the observation plane and a circle of a distance r+dr and the area da of the region (where $da=2\pi r \cdot dr$) that are determined based on a scanning electron microscope image in which a plane within the composite material is assumed to be the observation plane, the radial distribution function g(r) is calculated by formula (1) below:

$$g(r)=\{1/<\rho>\}\times\{dn/da\} \quad (1).$$

Preferably, in the composite material described above, in terms of ease of handling of the composition before being cured when the composite material is used as a dental material (in particular, a dental filling restorative material), and the color tone and the contrast ratio of the composite material serving as the cured product, the total content of the identical particle diameter spherical particle group with respect to 100 parts by mass of the resin matrix is 10 to 1500 parts by mass, and the content of the superfine particle group with respect to 100 parts by mass of the resin matrix is 0.1 to 50 parts by mass. Moreover, preferably, the average primary particle diameter of all the identical particle diameter spherical particle groups included in the inorganic particles falls within a range of 230 to 1000 nm, and the average primary particle diameter of the superfine particle group falls within a range of 3 to 75 nm. Furthermore, preferably, $\Delta n$ (defined as a difference $(n_{(G-PIDm)}-n_{(MX)})$ between $n_{(MX)}$ and $n_{(G-PIDm)}$) is 0.001 to 0.1 for any $n_{(G-PIDm)}$.

A second aspect of the present invention is a dental filling restorative material which is formed of the composite material in the first aspect of the present invention.

A third aspect of the present invention is a curable composition for producing the composite material in the first aspect of the present invention, the curable composition including: a polymerizable monomer; inorganic particles; and a polymerization initiator,
the inorganic particles including:
an identical particle diameter spherical particle group (G-PID) which is formed with an aggregate of inorganic spherical particles having a predetermined average primary particle diameter within a range of 100 to 1000 nm and in which in the number-based particle size distribution of the aggregate, 90% or more of all the particles are present within a range of plus or minus 5% of the predetermined average primary particle diameter; and
a superfine particle group (G-SFP) that is formed with inorganic particles whose average primary particle diameter is less than 100 nm,
the number of the identical particle diameter spherical particle groups included in the inorganic particles is one or more,
when the number of the identical particle diameter spherical particle groups included in the inorganic particles is assumed to be a, and each of the identical particle diameter spherical particle groups are represented as $G-PID_m$ (where when a is 1, m is 1 whereas when a is equal to or greater than 2, m is a natural number from 1 to a) respectively in ascending order of the average primary particle diameters thereof, the average primary particle diameters of each $G-PID_m$ differ from each other by 25 nm or more,
the average primary particle diameter of the superfine particle group is smaller than the average primary particle diameter of $G-PID_1$ by 25 nm or more and
when the refractive index of a cured product of the polymerizable monomer at 25° C. is assumed to be $n_{(MX)}$, and the refractive index of the inorganic spherical particles of each $G-PID_m$ at 25° C. is assumed to be $n_{(G-PIDm)}$, for any $n_{(G-PIDm)}$, a relationship of $n_{(MX)}<n_{(G-PIDm)}$ holds true.

Preferably, in the curable composition described above, since it is possible to reliably obtain the short-range order structure, at least part of the one or more identical particle diameter spherical particle groups include one type of identical particle diameter spherical particle group and a resin whose refractive index at 25° C. is less than the refractive index of the inorganic spherical particles of the one type of identical particle diameter spherical particle group at 25° C., and are included as an organic-inorganic composite filler which does not include an identical particle diameter spherical particle group other than the one type of identical particle diameter spherical particle group.

A fourth aspect of the present invention is a method for producing a curable composition which includes a polymerizable monomer, inorganic particles that satisfy conditions (i) to (iv) below and a polymerization initiator and which provides a cured product that produces a structural color of a predetermined color tone,
the method including a mixing step of mixing the polymerizable monomer, the inorganic particles and the polymerization initiator,
in the mixing step, mixing conditions are adopted in which it is confirmed, for a mixture obtained in the step, that the dispersed state of the inorganic particles in the cured product obtained by curing the mixture satisfies conditions (I) and (II) below, and the mixing is performed:

[Conditions which Need to be Satisfied by Inorganic Particles]

(i) the inorganic particles include an identical particle diameter spherical particle group (G-PID) which is formed with an aggregate of inorganic spherical particles having a predetermined average primary particle diameter within a range of 100 to 1000 nm and in which in the number-based particle size distribution of the aggregate, 90% or more of all the particles are present within a range of plus or minus 5% of the predetermined average primary particle diameter, and the number of identical particle diameter spherical particle groups is one or more;

(ii) when the number of the identical particle diameter spherical particle groups included in the inorganic particles is assumed to be a, and each of the identical particle diameter spherical particle groups are represented as $G-PID_m$ (where when a is 1, m is 1 whereas when a is equal to or greater than 2, m is a natural number from 1 to a) respectively in ascending order of the average primary particle diameters thereof, the average primary particle diameters of each $G\text{-PID}_m$ differ from each other by 25 nm or more;
(iii) when the refractive index of a cured product of the polymerizable monomer at 25° C. is assumed to be $n_{(MX)}$, and the refractive index of the inorganic spherical particles of each $G\text{-PID}_m$ at 25° C. is assumed to be $n_{(G\text{-}PIDm)}$, for any $n_{(G\text{-}PIDm)}$, a relationship of $n_{(MX)} < n_{(G\text{-}PIDm)}$ holds true;
(iv) the inorganic particles include a superfine particle group (G-SFP) that is formed with inorganic particles whose average primary particle diameter is less than 100 nm and is smaller than the average primary particle diameter of $G\text{-PID}_1$ by 25 nm or more;
[Conditions which Need to be Satisfied by Dispersed State]
(I) when a dimensionless number ($r/r_0$) which is standardized by dividing a distance r from the center of an arbitrary one of the inorganic spherical particles dispersed in the cured product of the mixture by the average particle diameter $r_0$ of all the inorganic spherical particles dispersed in the cured product of the mixture is assumed to be an x-axis, and a radial distribution function g(r) indicating a probability that another inorganic spherical particle is present at a point the distance r away from the center of the arbitrary inorganic spherical particle is assumed to be a y-axis, in a radial distribution function graph indicating a relationship of $r/r_0$ and g(r) which corresponds to r at that time, a closest particle-to-particle distance $r_1$ which is defined as r corresponding to the peak top of a peak closest to an origin among peaks appearing in the radial distribution function graph is a value that is 1 to 2 times the average particle diameter $r_0$ of all the inorganic spherical particles dispersed in the cured product of the mixture;
(II) when r corresponding to the peak top of a peak second closest to the origin among the peaks appearing in the radial distribution function graph is assumed to be a second closest particle-to-particle distance $r_2$, a local minimum value of the radial distribution function g(r) between the closest particle-to-particle distance $r_1$ and the second closest particle-to-particle distance $r_2$ is a value of 0.56 to 1.10.

Preferably, in the method for producing a curable composition described above, based on the average particle density $<\rho>$ of the inorganic spherical particles within an observation plane, the number do of inorganic spherical particles which are present in a region between a circle of a distance r from an arbitrary inorganic spherical particle within the observation plane and a circle of a distance r+dr and the area da of the region (where da=$2\pi r \cdot dr$) that are determined based on a scanning electron microscope image in which a plane within the cured product of the mixture is assumed to be the observation plane, the radial distribution function g(r) is calculated by formula (1) below:

$$g(r) = \{1/<\rho>\} \times \{dn/da\} \quad (1).$$

Preferably, in the method for producing a curable composition described above, a method for determining the mixing conditions adopted in the mixing step is a method of (a) or (b) below:
(a) the method in which, previously, on a curable composition having the same or substantially the same composition as the actually produced curable composition, a plurality of mixing conditions are changed and the mixing is performed, the radial distribution function g(r) in the cured product of the mixture obtained when the mixing is performed under each of the mixing conditions is checked so as to determine the mixing conditions which satisfy the conditions (I) and (II) and the same mixing conditions as the determined mixing conditions are adopted;
(b) the method in which part of the mixture obtained partway through and/or after completion of the mixing step is sampled, whether or not the dispersed state of the inorganic particles in the cured product of the sampled mixture satisfies the conditions (I) and (II) is checked and the mixing is continued until these conditions are satisfied.

Effects of the Invention

In the present invention, even when a fine filler is added, for example, in order to adjust the viscosity of a curable composition such as a CR before being cured and the contrast ratio of a cured product, it is possible to obtain the same effects as the cured product of the curable composition disclosed in Patent Document 2. Specifically, it is possible to obtain excellent effects in which (1) since dye substances or pigment substances are not used, the problem of chronological discoloration is unlikely to occur, in which (2) the cured product thereof can be colored in desired color tones within a wide range of color tones from a bluish transparent color tone to the color tones of yellow to red, which are the same colors as dentin colors (according to the average particle diameter of a spherical filler used), and in which moreover, (3) since the cured product can be made to have moderate transparency, when the cured product is used as a dental restorative material, the colors are easily harmonized with the colors of restored teeth, and without complicated shade taking and shade selection of the composite resin being performed, with one type of composite resin, the appearance of the restored teeth having a wide range of colors can be restored close to the appearance of natural teeth.

In the composite material of the present invention, since the dispersed state of the spherical filler which can achieve the effects described above can be checked with an electron microscope observation, for example, a correlation between production conditions such as the kneading conditions of raw materials and the dispersed state is checked, and thus it is possible to determine production conditions under which the effects can be reliably obtained, with the result that production yields can be enhanced.

Furthermore, when the composite material of the present invention includes a plurality of identical particle diameter spherical particle groups (G-PID), each G-PID produces a structural color of a color tone corresponding to the average particle diameter thereof, and thus by combination of the G-PID to be mixed, the entire color tone of produced colors can be controlled.

Although the mechanism which can obtain the excellent effects as described above is not always clear, it is inferred that the mechanism is provided because since the superfine particle group is so small as not to affect the dispersed state of the inorganic spherical particles and when a plurality of G-PID are included, a constant difference in the size of the average primary particle diameter thereof is produced, without the inorganic spherical particles belonging to different G-PID being substituted with each other, the inorganic spherical particles can be dispersed so as to have a short-range order structure capable of developing a structural color according to each G-PID.

PREFERRED MODE FOR CARRYING OUT THE INVENTION

<<Composite Material>>

Figure 1:
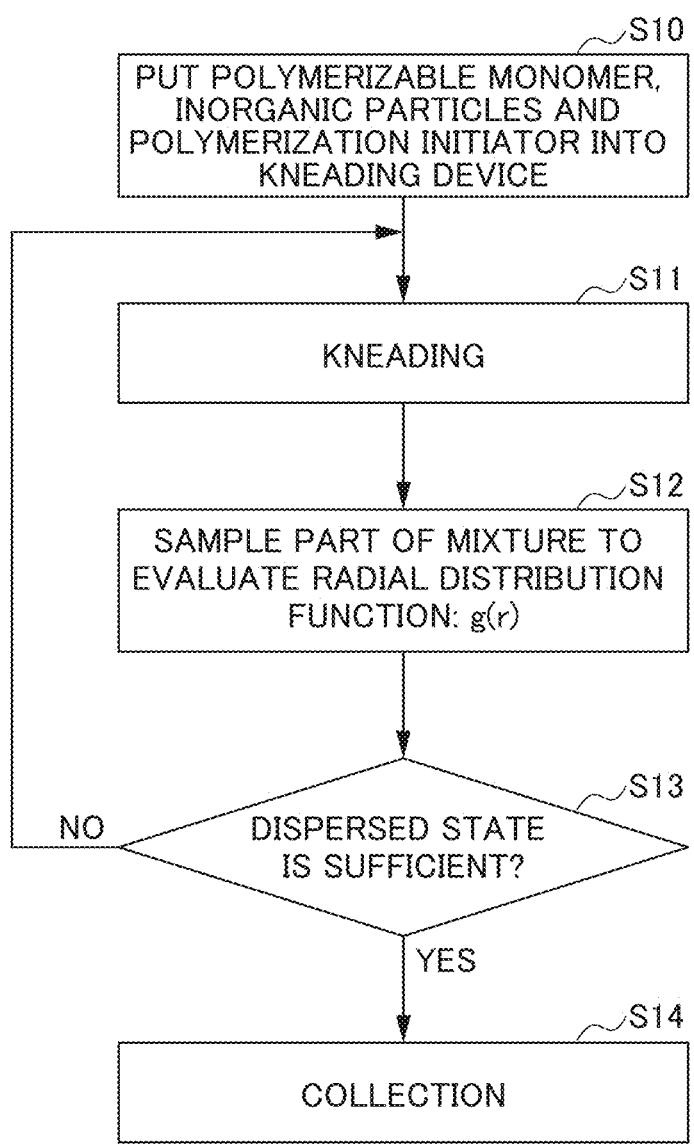
FIG. 1 is a flow diagram showing a method for producing a curable composition in the present embodiment.

The composite material of the present invention is a composite material in which inorganic particles are dispersed in a resin matrix, and has the following characteristics.

Firstly, the inorganic particles include: an identical particle diameter spherical particle group (G-PID) which is formed with an aggregate of inorganic spherical particles having a predetermined average primary particle diameter within a range of 100 to 1000 nm and in which in a number-based particle size distribution of the aggregate, 90% or more of all the particles are present within a range of plus or minus 5% of the predetermined average primary particle diameter; and a superfine particle group (G-SFP) that is formed with inorganic particles whose average primary particle diameter is less than 100 nm, and the number of identical particle diameter spherical particle groups included in the inorganic particles is one or more.

Secondly, when the number of the identical particle diameter spherical particle groups included in the inorganic particles is assumed to be a, and each of the identical particle diameter spherical particle groups are represented as G-PID$_m$ (where when a is 1, m is 1 whereas when a is equal to or greater than 2, m is a natural number from 1 to a) respectively in ascending order of the average primary particle diameters thereof, the average primary particle diameters of each G-PID$_m$ differ from each other by 25 nm or more, and the average primary particle diameter of the superfine particle group is smaller than the average primary particle diameter of G-PID$_1$ (whose average primary particle diameter is the smallest) by 25 nm or more.

Thirdly, when the refractive index of the resin matrix at 25° C. is assumed to be n$_{(MX)}$, and the refractive index of the inorganic spherical particles of each G-PID$_m$ at 25° C. is assumed to be n$_{(G-PIDm)}$, for any n$_{(G-PIDm)}$, a relationship of n$_{(MX)}$<n$_{(G-PIDm)}$ holds true.

Fourthly, the arrangement structure of the inorganic spherical particles of all the identical particle diameter spherical particle groups in the resin matrix has a short-range order structure which satisfies conditions 1 and 2 below.

[Condition 1] When a dimensionless number (r/r$_0$) which is standardized by dividing a distance r from the center of an arbitrary one of the inorganic spherical particles dispersed in the composite material by the average particle diameter r$_0$ of all the inorganic spherical particles dispersed in the composite material is assumed to be an x-axis, and a radial distribution function g(r) indicating a probability that another inorganic spherical particle is present at a point the distance r away from the center of the arbitrary inorganic spherical particle is assumed to be a y-axis, in a radial distribution function graph indicating a relationship of r/r$_0$ and g(r) which corresponds to r at that time, a closest particle-to-particle distance r$_1$ which is defined as r corresponding to the peak top of a peak closest to an origin among peaks appearing in the radial distribution function graph is a value that is 1 to 2 times the average particle diameter r$_0$ of all the inorganic spherical particles dispersed in the composite material.

[Condition 2] When r corresponding to the peak top of a peak second closest to the origin among the peaks appearing in the radial distribution function graph is assumed to be a second closest particle-to-particle distance r$_2$, a local minimum value of the radial distribution function g(r) between the closest particle-to-particle distance r$_1$ and the second closest particle-to-particle distance r$_2$ is a value of 0.56 to 1.10.

Although the composite material according to the present embodiment basically falls into the category of the cured product of the curable composition disclosed in Patent Document 2, the composite material according to the present embodiment is newly characterized in that the dispersed state of the inorganic spherical particles is identified so as to reliably obtain the effects described above, that with respect to the inorganic filler which is an arbitrary component in the curable composition of Patent Document 2 and which is one of the "other additives", an inorganic filler whose particle diameter does not adversely affect the effects described above is included and that it is confirmed that a plurality of types of the identical particle diameter spherical particle groups described above can be included. Hence, a polymerizable monomer serving as the raw material of the resin matrix and the individual identical particle diameter spherical particle groups, and more specifically, the average primary particle diameter thereof and the number-based particle size distribution in the corresponding G-PID, the shape, the material, the refractive index, and the like of the inorganic spherical particles of the G-PID, a polymerization initiator used for obtaining the cured product and the like may be the same as in the curable composition of Patent Document 2.

Hence, the fourth characteristic point regarding the identification of the dispersed state of the inorganic spherical particles will first be described, and then various types of raw materials used in the composite material according to the present embodiment, a production method, and the like will be described.

In the composite material according to the present embodiment, as a method of quantifying the dispersed state of the inorganic spherical particles, the "radial distribution function g(r) within a plane" which is disclosed in Patent Document 1 is used, and thus the short-range order structure is defined. Here, as found from the use of the radial distribution function g(r) in Patent Document 1, the radial distribution function g(r) is well known as a function for determining a probability that another particle is present at a point only a distance r away from an arbitrary particle, and is defined by formula (1) below.

$$g(r) = \{1/<\rho>\} \times \{dn/da\} \quad (1)$$

In formula (1) described above, <ρ> represents the average particle density of particles within the plane, do represents the number of particles which are present in a region between a circle having a radius r and a circle having a radius r+dr respectively with an arbitrary particle within the plane being the center and da represents $2\pi r \cdot dr$, which is the area of the region described above.

In general, the radial distribution function g(r) is represented by a radial distribution function graph in which a distance r is taken along an x-axis (distance axis) and in which the value of g(r) at r (the result of a calculation by formula (1) described above) is taken along a y-axis (vertical axis) or a radial distribution function graph (see FIGS. 3 to 7) in which a dimensionless number that is standardized by dividing r by the average particle diameter of the particles is taken along a distance axis and in which the value of g(r) at r corresponding to the value of the x-axis (the result of a calculation by the formula described above) is taken along a y-axis (vertical axis).

In the present embodiment, since $<\rho>$ and dn are confirmed easily and reliably, based on $<\rho>$, dn and da ($=2\pi r \cdot dr$) (corresponding to the value of dr adopted when dn described above is determined) that are determined based on a scanning electron microscope image in which a plane within the composite material according to the present embodiment is assumed to be an observation plane, g(r) calculated by formula (1) described above is preferably adopted.

The determination of $<\rho>$, dn and da can be performed as follows. The composite material according to the present embodiment is first produced, for example, by curing the curable composition, and by a means such as the polishing of the surface of the obtained composite material, the plane (observation plane) on which the dispersed state of the inorganic spherical particles within the composite material can be observed is exposed on the surface. Then, the observation plane is observed with a scanning electron microscope, and thus a microscope image of a region in which at least 500 or more inorganic spherical particles are contained within the plane is acquired. Thereafter, for the obtained scanning electron microscope image, with image analysis software (for example, "Simple Digitizer ver. 3.2" free software), coordinates of the inorganic spherical particles within the region are determined. The coordinates of an arbitrary inorganic spherical particle are selected from obtained coordinate data, with the selected inorganic spherical particle being the center, a circle in which at least 200 or more inorganic spherical particles are included and in which a distance r is the radius is drawn and the number of inorganic spherical particles included within the circle is counted, with the result that the average particle density $<\rho>$ (unit: pieces/cm$^2$) can be determined.

With respect to dn, dr, whose length is a value of about $r_0/100$ to $r_0/10$ when the average particle diameter of the inorganic spherical particles is represented as $r_0$, is set, one inorganic spherical particle which is arbitrarily selected is assumed to be a central particle, the number of inorganic spherical particles included within a region between a circle in which a distance r from the center thereof is the radius and a circle which has the same center as the circle described above and which has a radius r+dr is counted and thus dn can be determined. Furthermore, da, which is the area of the region between the two circles, is determined as $2\pi r \cdot dr$ based on the length of dr, which is actually set.

In the composite material according to the present embodiment, when the dimensionless number ($r/r_0$) which is standardized by dividing the distance r from the center of an arbitrary one of the inorganic spherical particles dispersed in the composite material by the average particle diameter $r_0$ of all the inorganic spherical particles dispersed in the composite material is assumed to be the x-axis, and the radial distribution function g(r) indicating the probability that another inorganic spherical particle is present at the point the distance r away from the center of the arbitrary inorganic spherical particle is assumed to be the y-axis, in the radial distribution function graph indicating the relationship of $r/r_0$ and g(r) which corresponds to r at that time, the closest particle-to-particle distance $r_1$ which is defined as r corresponding to the peak top of the peak closest to the origin among the peaks appearing in the radial distribution function graph needs to be the value that is 1 to 2 times the average particle diameter $r_0$ of all the inorganic spherical particles dispersed in the composite material (Condition 1). When $r_1$ is less than one times $r_0$ ($r_1/r_0<1$), the amount of overlap of the particles within the plane is increased whereas when $r_1$ is greater than two times $r_0$ ($r_1/r_0>2$), particles are not present in the vicinity of the selected inorganic particle in the center, and thus the short-range order disappears, with the result that a structural color is prevented from being developed. In other words, since the short-range order is maintained and a structural color is easily developed, $r_1/r_0$ is 1.0 to 2.0 and is preferably 1.0 to 1.5.

In the composite material according to the present embodiment, when r corresponding to the peak top of the peak second closest to the origin among the peaks appearing in the radial distribution function graph is assumed to be the second closest particle-to-particle distance $r_2$, the local minimum value of the radial distribution function g(r) between the closest particle-to-particle distance $r_1$ and the second closest particle-to-particle distance $r_2$ also needs to be a value of 0.56 to 1.10 (Condition 2). When the local minimum value described above is less than 0.56, the long-range order of the arrangement structure of the inorganic spherical particles is increased, and thus not only the incident angle dependence of light of a structural color which is developed is increased, but also the chroma of the composite material is increased, with the result that when the composite material is used as a dental filling material, it is difficult to obtain color tone compatibility. On the other hand, when the local minimum value described above exceeds 1.10, the arrangement structure of the inorganic spherical particles is a random structure, and thus it is difficult to obtain intended reflection performance, with the result that a desired structural color is unlikely to be developed. In other words, since a structural color is developed, and the color tone compatibility of the composite material serving as a dental filling material is easily obtained, the local minimum value described above is a value of 0.56 to 1.10 and is preferably a value of 0.56 to 1.00.

It is confirmed from the examination of the present inventors that in the curable composition (CR) disclosed in Patent Document 2, depending on conditions under which individual components are kneaded so as to prepare the composition (CR), even at an extremely low frequency, desired effects are not obtained, and that when the radial distribution function g(r) is evaluated for such a system that the effects as described above cannot be obtained, Condition 1 and/or Condition 2 are not satisfied. This means that the arrangement structure of the inorganic spherical particles of the identical particle diameter spherical particle groups (G-PID) in the composite material according to the present embodiment correlates with production conditions such as raw material kneading conditions. In other words, when as in manual kneading, variations in kneading conditions are easily produced, a case where kneading conditions are insufficient occurs with a certain probability, Condition 1 or Condition 2 is not satisfied, and thus intended color tone compatibility is not obtained, with the result that yields at the time of production are lowered. By contrast, kneading is performed with a kneader under controlled conditions, and, for example, defoaming treatment is added so as to prevent air bubbles from being included in the composite material, with the result that it is possible to reliably satisfy Condition 1 and condition 2.

Next, various types of raw materials used in the composite material according to the present embodiment, the production method, and the like will be described.

<Resin Matrix>

The resin matrix in the composite material according to the present embodiment is not particularly limited as long as the resin matrix is formed of a resin in which the inorganic spherical particles can be present so as to be dispersed. Although as the resin matrix, a thermoplastic resin or the like can also be used, since it is easy to control the dispersed state of the inorganic spherical particles, the resin matrix is preferably formed of the cured product of a curable composition in which a polymerizable monomer is a main component. Furthermore, in terms of ease of handling when the resin matrix is used as a dental filling restorative material and physical properties (mechanical properties and adhesion to a tooth substance in a dental application), the cured product of a curable composition in which a radical polymerizable monomer or a cationic polymerizable monomer is a main component is more preferable. Since a condition regarding the refractive index, that is, a condition of $n_{(MX)} < n_{(G-PIDm)}$ is easily satisfied, the cured product of a curable composition in which the refractive index of the cured product at 25° C. is 1.40 to 1.57; in particular 1.42 to 1.57, is further preferable.

[Polymerizable Monomer]

As a radical polymerizable monomer which can be used to obtain the resin matrix, a (meta)acrylic compound can be mentioned. As a cationic polymerizable monomer which can be used to obtain the resin matrix, epoxies and oxetanes can be mentioned. Examples of the (meta)acrylic compound which can be suitably used include compounds shown in (I) to (IV) below.

(I) Monofunctional Polymerizable Monomer
(I-i) Compound that does not have an Acidic Group and a Hydroxy Group methyl (meth)acrylate, ethyl (meth)acrylate, n-butyl (meth)acrylate, 2-ethylhexyl (meth) acrylate, n-lauryl (meth) acrylate, n-stearyl (meth) acrylate, tetrafurfuryl (meth) acrylate, glycidyl (meth) acrylate, methoxyethylene glycol (meth)acrylate, methoxydiethylene glycol (meth) acrylate, methoxytriethylene glycol (meth) acrylate, methoxypolyethylene glycol (meth) acrylate, ethoxyethylene glycol (meth)acrylate, ethoxydiethylene glycol (meth) acrylate, ethoxytriethylene glycol (meth) acrylate, ethoxypolyethylene glycol (meth)acrylate, phenoxyethylene glycol (meth)acrylate, phenoxydiethylene glycol (meth) acrylate, phenoxytriethylene glycol (meth)acrylate, phenoxypolyethylene glycol (meth)acrylate, cyclohexyl (meth)acrylate, benzyl (meth) acrylate, isobornyl (meth) acrylate, trifluoroethyl (meth)acrylate, and the like.

(I-ii) Compound that has an Acidic Group (meth)acrylic acid, N-(meth)acryloyl glycine, N-(meth) acryloyl aspartic acid, N-(meth)acryloyl-5-aminosalicylic acid, 2-(meth)acryloyloxyethyl hydrogen succinate, 2-(meth)acryloyloxyethyl hydrogen phthalate, 2-(meth) acryloyloxyethyl hydrogen malate, 6-(meth)acryloyloxyethyl naphthalene-1,2,6-tricarboxylic acid, O-(meth)acryloyl tyrosine, N-(meth)acryloyl tyrosine, N-(meth)acryloyl phenylalanine, N-(meth)acryloyl-p-aminobenzoic acid, N-(meth)acryloyl-o-aminobenzoic acid, p-vinylbenzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosailcylic acid and compounds obtained by converting carboxy groups of these compounds to acid anhydride groups; 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth) acryloyloxyethyl-3'-methacryloyloxy-2'-(3,4-dicarboxybenzoyloxy) propyl succinate, 4-(2-(meth)acryloyloxyethyl) trimellitate anhydride, 4-(2-(meth)acryloyloxyethyl) trimellitate, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 4-(meth) acryloyloxybutyl trimellitate, 6-(meth)acryloyloxyethyl naphthalene-1,2,6-tricarboxylic acid anhydride, 6-(meth) acryloyloxyethyl naphthalene-2,3,6-tricarboxylic acid anhydride, 4-(meth)acryloyloxyethylcarbonylpropionoyl-1,8-naphthalic anhydride, 4-(meth) acryloyloxyethylnaphthalene-1,8-tricarboxylic acid anhydride, 9-(meth)acryloyloxynonane-1,1-dicarboxylic acid, 13-(meth)acryloyloxytridecane-1,1-dicarboxylic acid, 11-(meth)acrylamidoundecane-1,1-dicarboxylic acid, 2-(meth)acryloyloxyethyl dihydrogen phosphate, 2-(meth) acryloyloxyethylphenyl hydrogen phosphate, 10-(meth) acryloyloxydecyl dihydrogen phosphate, 6-(meth)acryloyloxyhexyl dihydrogen phosphate, 2-(meth) acryloyloxyethyl-2-bromoethyl hydrogen phosphate, 2-(meth)acrylamidoethyl dihydrogen phosphate, 2-(meth) acrylamido-2-methylpropanesulfonic acid, 10-sulfodecyl (meth) acrylate, 3-(meth)acryloxypropyl-3-phosphonopropionate, 3-(meth)acryloxypropyl phosphonoacetate, 4-(meth)acryloxybutyl-3-phosphonopropionate, 4-(meth) acryloxybutyl phosphonoacetate, 5-(meth)acryloxypentyl-3-phosphonopropionate, 5-(meth)acryloxypentyl phosphonoacetate, 6-(meth)acryloxyhexyl-3-phosphonopropionate, 6-(meth)acryloxyhexyl phosphonoacetate, 10-(meth)acryloxydecyl-3-phosphonopropionate, 10-(meth)acryloxydecyl phosphonoacetate, 2-(meth)acryloxyethyl-phenyl phosphonate, 2-(meth)acryloyloxyethylphosphonic acid, 10-(meth) acryloyloxydecylphosphonic acid, N-(meth)acryloyl-co-aminopropylphosphonic acid, 2-(meth) acryloyloxyethylphenyl hydrogen phosphate, 2-(meth) acryloyloxyethyl-2'-bromoethyl hydrogen phosphate, 2-(meth)acryloyloxyethylphenyl phosphonate, and the like.

(I-iii) Compound that has a Hydroxy Group 2-hydroxyethyl (meth) acrylate, 3-hydroxypropyl (meth) acrylate, 4-hydroxybutyl (meth) acrylate, 6-hydroxyhexyl (meth) acrylate, 10-hydroxydecyl (meth) acrylate, propylene glycol mono(meth)acrylate, glycerol mono(meth)acrylate, erythritol mono(meth)acrylate, N-methylol (meth)acrylamide, N-hydroxyethyl (meth) acrylamide, N,N-(dihydroxyethyl) (meth)acrylamide, and the like.

(II) Bifunctional Polymerizable Monomer
(II-i) Aromatic Compound-Based Monomer 2,2-bis(methacryloyloxyphenyl)propane, 2,2-bis[(3-methacryloyloxy-2-hydroxypropyloxy)phenyl]propane, 2,2-bis(4-methacryloyloxyphenyl)propane, 2,2-bis(4-methacryloyloxypolyethoxyphenyl)propane, 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacryloyloxydiethoxyphenyl)-2(4-methacryloyloxytriethoxyphenyl)propane, 2(4-methacryloyloxydipropoxyphenyl)-2-(4- methacryloyloxytriethoxyphenyl)propane, 2,2-bis(4-methacryloyloxypropoxyphenyl)propane, 2,2-bis(4-methacryloyloxyisopropoxyphenyl)propane and acrylates corresponding to these methacrylates; diadducts obtainable from addition of vinyl monomers having an —OH group, such as methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds having an aromatic group, such as methylbenzene diisocyanate and 4,4'-diphenylmethane diisocyanate; di(methacryloxyethyl)diphenylmethanediurethane, and the like.

(II-ii) Aliphatic Compound-Based Monomer

Ethylene glycol dimethacrylate, diethylene glycol dimethacrylate, triethylene glycol dimethacrylate, tetraethylene glycol dimethacrylate, neopentyl glycol dimethacrylate, 1,3-butanediol dimethacrylate, 1,4-butanediol dimethacrylate, 1,6-hexanediol dimethacrylate and acrylates corresponding to these methacrylates; diadducts obtainable from addition products of vinyl monomers having an —OH group, including methacrylates such as 2-hydroxyethyl methacrylate, 2-hydroxypropyl methacrylate, and 3-chloro-2-hydroxypropyl methacrylate, or acrylates corresponding to these methacrylates, and diisocyanate compounds such as hexamethylene diisocyanate, trimethylhexamethylene diisocyanate, methylcyclohexane diisocyanate, isophorone diisocyanate, and methylenebis(4-cyclohexyl isocyanate), for example, 1,6-bis(methacrylethyloxycarbonylamino)trimethylhexane; 1,2-bis(3-methacryloyloxy-2-hydroxypropoxy)ethyl, and the like.

(III) Trifunctional Polymerizable Monomer

Methacrylates such as trimethylolpropane trimethacrylate, trimethylolethane trimethacrylate, pentaerythritol trimethacrylate and trimethylolmethane trimethacrylate, acrylates corresponding to these methacrylates, and the like.

(IV) Tetrafunctional Polymerizable Monomer

Pentaerythritol tetramethacrylate, pentaerythritol tetraacrylate; diadducts obtainable from addition products of diisocyanate compounds such as methylbenzene diisocyanate, methylcyclohexane diisocyanate, isophorone diisocyanate, hexamethylene diisocyanate, trimethylhexamethylene diisocyanate, methylenebis(4-cyclohexyl isocyanate), 4,4-diphenylmethane diisocyanate and tolylene-2,4-diisocyanate and glycidol dimethacrylate, and the like.

With respect to these (meth)acrylate-based polymerizable monomers, a plurality of types thereof may be used in combination as necessary.

Furthermore, as necessary, a polymerizable monomer other than the (meth)acrylate-based monomers described above may be used.

As the polymerizable monomer, a plurality of types of polymerizable monomers are generally used in order to adjust the physical properties (mechanical properties and adhesion to a tooth substance in a dental application) of the cured product serving as the resin matrix. At that time, it is desirable to set the types and the amounts of polymerizable monomers such that the refractive index of the polymerizable monomer (which may be a mixture) at 25° C. falls within a range of 1.38 to 1.55 because the condition regarding the refractive index is easily satisfied. That is, when a silica-titanium group element oxide-based composite oxide whose refractive index is easily adjusted as the inorganic spherical particles is used, though the refractive index thereof at 25° C. falls within a range of about 1.45 to 1.58 depending on the content of silica, the refractive index of the polymerizable monomer (which may be a mixture) is set to fall into a range of 1.38 to 1.55, and thus the refractive index of the cured product to be obtained can be adjusted to fall into a range of about 1.40 to 1.57, with the result that it is easy to satisfy the condition described above. The refractive indexes of the polymerizable monomer and the cured product of the polymerizable monomer can be determined with an Abbe refractometer at 25° C.

<Inorganic Particles>

The inorganic particles dispersed in the resin matrix in the composite material according to the present embodiment include one or more identical particle diameter spherical particle groups (G-PID) and the superfine particle group (G-SFP).

[Identical Particle Diameter Spherical Particle Group G-PID]

The identical particle diameter spherical particle group G-PID is formed with the aggregate of the inorganic spherical particles having the predetermined average primary particle diameter within a range of 100 to 1000 nm, in the number-based particle size distribution of the aggregate, 90% or more of all the particles are present within the range of plus or minus 5% of the predetermined average primary particle diameter and the identical particle diameter spherical particle group G-PID means the aggregate described above. The individual inorganic spherical particles of the aggregate are formed of substantially the same substance.

Here, with respect to the average primary particle diameter of the inorganic spherical particles, a photograph of G-PID is shot with a scanning electron microscope, 30 or more particles which are observed within a unit field of view of the photogram are selected, the respective primary particle diameters (maximum diameters) thereof are determined, and the average primary particle diameter of the inorganic spherical particles means the average value of the determined primary particle diameters. The term "spherical" may be "substantially spherical", and it is not always necessary to provide a completely true sphere. The photograph of G-PID is shot with the scanning electron microscope, the maximum diameters of respective particles (30 or more particles) within a unit field of view thereof are measured, the average uniformity is obtained by dividing particle diameters orthogonal to the maximum diameters by the maximum diameters and the average uniformity is equal to or greater than 0.6 and preferably equal to or greater than 0.8.

In the composite material according to the present embodiment, each of the constituent particles of G-PID, which is the aggregate of the inorganic particles which are spherical and whose particle diameter distribution (number-based particle size distribution) is narrow, have a specific short-range order structure so as to be dispersed in the resin matrix; and thus diffractive interference occurs according to Bragg conditions and light of a specific wavelength is emphasized, with the result that colored light of a color tone corresponding to the average primary particle diameter is produced (structural color is developed). In other words, in order to develop a structural color, 90% (pieces) or more of the inorganic spherical particles of G-PID need to be present within a range of plus or minus 5% of the average particle diameter. In order to develop a structural color having a specific color tone within a wide range of bluish-yellowish-reddish colors, the average primary particle diameter of the inorganic spherical particles of G-PID needs to fall within a range of 100 to 1000 nm. In a case where spherical particles whose average primary particle diameter is less than 100 nm are used, the phenomenon of interference of visible light is unlikely to occur, and a structural color is unlikely to be developed. On the other hand, in a case where spherical particles whose average primary particle diameter is greater than 1000 nm are used, though the development of the phenomenon of interference of light can be expected, it is not preferable that the composite material according to the present embodiment is used as a dental filling restorative material because the spherical particles settle down or the polishing property is lowered.

When the average primary particle diameter is 230 to 800 nm, a yellowish-reddish structural color (colored light) is easily developed, whereas when the average primary particle diameter is equal to or greater than 150 nm and less than 230 nm, a bluish structural color (colored light) is easily developed.

Since a yellowish-reddish structural color (colored light) which is preferable for a dental filling restorative material is developed, the average primary particle diameter of G-PID is preferably 230 to 800 nm, more preferably 240 to 500 nm and further preferably 260 to 350 nm. When G-PID whose average primary particle diameter is equal to or greater than 230 nm and less than 260 nm is used, colored light which is obtained is yellowish, and the composite material is useful for the restoration of teeth in the class of B system (reddish yellow) in a shade guide ("VITA Classical", made by Vita Zahnfabrik H. Rauter GmbH & Co. KG), and is particularly useful for the restoration of a cavity formed over from the enamel to the dentine. When G-PID whose average primary particle diameter is in a range of 260 to 350 nm is used, colored light which is obtained is reddish, and the composite material is useful for the restoration of teeth in the class of A system (reddish brown) in the shade guide ("VITA Classical", made by Vita Zahnfabrik H. Rauter GmbH & Co. KG), and is particularly useful for the restoration of a cavity formed over from the enamel to the dentine. Since the color phase of the dentine is often reddish, when only G-PID whose average primary particle diameter is in a range of 260 to 350 nm is used, the composite material is most preferable because compatibility with restored teeth having a variety of color tones is widely enhanced. On the other hand, when only G-PID whose average primary particle diameter is equal to or greater than 150 nm and less than 230 nm is used, though colored light which is obtained is bluish, and the color tone compatibility with the tooth substance is likely to be poor in a cavity formed over from the enamel to the dentine, the composite material is useful for the restoration of the enamel and is particularly useful for the restoration of an incisal portion.

The number of types of G-PID included in the inorganic particles dispersed in the resin matrix in the composite material according to the present embodiment may be one or more. The number a of G-PID included is preferably 1 to 5, more preferably 1 to 3 and further preferably 1 or 2. When a plurality of types of G-PID are included in the inorganic particles, the inorganic spherical particles of each G-PID may be formed of the same substance as each other or may be formed of different substances.

When a plurality of types of G-PID are included in the inorganic particles, the average primary particle diameters of each G-PID need to differ from each other by 25 nm or more. In other words, when the number of G-PID included in the inorganic particles is assumed to be a (for example, a=3), G-PID here are each represented as G-PID$_m$ (where when a is 1, m is 1 whereas when a is equal to or greater than 2, m is a natural number from 1 to a) respectively in ascending order of the average primary particle diameters thereof and the average primary particle diameters of each G-PID$_m$ are assumed to be d$_m$ respectively, each d$_m$ needs to differ from one another by 25 nm or more. For example, when a=3, it is necessary that $|d_1-d_2|\geq 25$ nm and $|d_2-d_3|\geq 25$ nm (naturally, a relationship of $|d_1-d_3|\geq 25$ nm holds true). This condition is satisfied, and thus, for example, a specific structural color can be developed according to each G-PID (the average particle diameter). It is inferred that this is because, for example, each G-PID is dispersed in the form of a coagulated material in which a small number of inorganic spherical particles that do not exceed about 20 pieces are coagulated with a very loose bonding force, and thus G-PID can be dispersed so as to have a short-range order structure capable of developing a structural color according to each G-PID. By contrast, when this condition is not satisfied, a structural color is unlikely to be developed. It is considered that this is because the particle diameter distribution of all the inorganic spherical particles is broad, thus the inorganic spherical particles of each G-PID are substituted with each other so as to be dispersed and the same phenomenon occurs as in the case where an aggregate of a single type of inorganic spherical particles which do not satisfy the condition of the number-based particle size distribution is used.

When a plurality of types of G-PID are included in the composite material according to the present embodiment, the average primary particle diameters d$_m$ of each G-PID$_m$ preferably differ from each other by 30 nm or more, and more preferably differ from each other by 40 nm or more. In other words, a difference between d$_m$ and d$_{m-1}$ is preferably equal to or greater than 30 nm, and more preferably equal to or greater than 40 nm. A difference between d$_m$ and d$_{m-1}$ is preferably equal to or less than 100 nm, and more preferably equal to or less than 60 nm.

When a plurality of types of each G-PID are included in the composite material according to the present embodiment, since each G-PID has a very sharp particle size distribution and the difference described above is produced between the average primary particle diameters, the particle size distributions of G-PID are unlikely to overlap each other, and even when they overlap each other, the particle size distribution of each G-PID can be checked. In other words, the particle size distribution of the inorganic particles included in the composite material according to the present embodiment has the same number of independent peaks as the number of G-PID included in the composite material in a range of 100 to 1000 nm, and even when a part of each of the peaks overlaps, waveform processing is performed so as to be able to check the average primary particle diameters of each G-PID and the number-based particle size distribution. The particle size distribution of the inorganic particles included in the present invention can also be checked, for example, by performing image processing on an electron microscope photogram of an internal surface of the composite material according to the present embodiment.

(Inorganic Spherical Particles)

As long as the above-described condition for formation of G-PID is satisfied, the material of the inorganic spherical particles of G-PID is not particularly limited. Examples of the material which can be suitably used include particles formed of amorphous silica, silica-titanium group element oxide-based composite oxide particles (such as silica-zirconia and silica-titania), quartz, alumina, barium glass, strontium glass, lanthanum glass, fluoroaluminosilicate glass, ytterbium fluoride, zirconia, titania, colloidal silica, and the like. Among them, since the refractive index is easily adjusted, particles formed of silica-titanium group element oxide-based composite oxide are preferably used.

Here, the silica-titanium group element oxide-based composite oxide particles mean a composite oxide of silica and a titanium group element (element of Group 4 in the periodic table) oxide, and the refractive index thereof at 25° C. can be changed in a range of about 1.45 to 1.58 according to the content of silica. Specific examples of the silica-titanium group element oxide-based composite oxide particles include silica-titania, silica-zirconia, silica-titania-zirconia, and the like. Among these, since high X-ray opacity can be provided, silica-zirconia is preferable. Although the composite ratio of silica-zirconia is not particularly limited, since sufficient X-ray opacity is provided and the refractive index is made to fall into a suitable range which will be described later, it is preferable that the content of silica be 70 to 95 mol % and that the content of the titanium group element oxide be 5 to 30 mol %.

In these silica-titanium group element oxide-based composite oxide particles, compounding of a metal oxide other than silica and a titanium group element oxide is also allowed as long as the amount thereof is small. Specifically, an alkali metal oxide such as sodium oxide or lithium oxide may be contained as long as the content thereof is 10 mol % or less.

Although a method for producing the silica-titanium group element oxide-based composite oxide particles is not particularly limited, in order to obtain a spherical filler, for example, a so-called sol-gel method of adding a mixed solution including a hydrolyzable organosilicon compound and a hydrolyzable organotitanium group metal compound to an alkaline solvent, performing hydrolysis and precipitating a reaction product is suitably adopted.

The inorganic spherical particles formed of the silica-titanium group element oxide-based composite oxide may be surface-treated with a silane coupling agent. The surface treatment is performed with the silane coupling agent, and thus when the inorganic spherical particles are formed into an organic-inorganic composite filler which will be described later, excellent interfacial strength with the organic resin matrix of the organic-inorganic composite filler is provided. Typical examples of the silane coupling agent include organosilicon compounds such as γ-methacryloyloxyalkyltrimethoxysilane and hexamethyldisilazane. The amount of surface treatment with the silane coupling agent is not particularly limited, and although an optimal value may be determined after the mechanical properties and the like of the cured product of the obtained curable composition are previously checked by experiments, an example of a suitable range is a range of 0.1 parts by mass to 15 parts by mass with respect to 100 parts by mass of the spherical particles.

(Relationship Between Refractive Index of Resin Matrix and Refractive Index of Inorganic Spherical Particles)

In the composite material according to the present embodiment, when the refractive index of the resin matrix at 25° C. is assumed to be $n_{(MX)}$, and the refractive index of the inorganic spherical particles of each G-PID$_m$ at 25° C. is assumed to be $n_{(G-PIDm)}$, for any $n_{(G-PIDm)}$, a relationship of $n_{(MX)} < n_{(G-PIDm)}$ needs to hold true. In a case where the relationship described above is not satisfied, even when a structural color is developed, light of a short wavelength is easily scattered in the resin matrix, and thus it is difficult to confirm the developed structural color. In terms of the visibility and clarity of the developed structural color and color tone compatibility when the composite material is used as a dental filling restorative material, for $n_{(G-PIDm)}$, $\Delta n$ ($=n_{(G-PIDm)}-n_{(MX)}$) which is a difference between $n_{(G-PIDm)}$ and $n_{(MX)}$ is preferably 0.001 to 0.1, more preferably 0.002 to 0.1 and further preferably 0.005 to 0.05.

As described above, the refractive index of the polymerizable monomer (which may be a mixture) at 25° C. is set in a range of 1.38 to 1.55, and thus the refractive index ($n_{(MX)}$) of the cured product of the resin matrix at 25° C. can be made to fall into a range of 1.40 to 1.57. As described above, the content of silica is changed, and thus the refractive index ($n_{(G-PIDm)}$) of the silica-titanium group element oxide-based composite oxide at 25° C. can be changed in a range of about 1.45 to 1.58. Hence, these relationships are utilized, and thus $\Delta n$ can easily be made to fall into a suitable range.

[Superfine Particle Group G-SFP]

The superfine particle group (G-SFP) is a particle aggregate formed with the inorganic particles whose average particle diameter is less than 100 nm, and is mixed, for example, in order to adjust the viscosity of the curable composition serving as a precursor (material which is cured to obtain the composite material) of the composite material according to the present embodiment or to adjust the contrast ratio of the composite material according to the present embodiment. However, the average primary particle diameter of G-SFP needs to be smaller, by 25 nm or more, than the average primary particle diameter ($d_1$) of G-PID$_1$ whose average primary particle diameter is the smallest among the G-PID to be mixed in the inorganic particles. When the condition as described above is not satisfied, the dispersed state of the inorganic spherical particles is adversely affected, and thus a structural color is unlikely to be developed. The shape of the inorganic particles of G-SFP is not particularly limited, and may be irregular shape or spherical. The lower limit of the average primary particle diameter is normally 2 nm.

Since the development of a structural color is little affected, the average primary particle diameter of G-SFP is preferably 3 to 75 nm, and more preferably 5 to 50 nm. For the same reason, the average primary particle diameter of G-SFP is preferably smaller than the average primary particle diameter ($d_1$) of G-PID$_1$ by 30 nm or more, and more preferably smaller than the average primary particle diameter ($d_1$) of G-PID$_1$ by 40 nm or more.

As the material of the inorganic particles of G-SFP, the same material as that of the inorganic spherical particles can be used without particular limitation. As in the inorganic spherical particles, the surface treatment can be performed with the silane coupling agent. The preferred form is basically the same as that of the inorganic spherical particles except the average primary particle diameter and the shape.

<<Relationship Between Composite Material and Curable Composition>>

The composite material according to the present embodiment can be suitably produced by polymerizing and curing the curable composition which will be described later. The mixing ratio of individual components in the composite material according to the present embodiment is substantially uniquely determined by the composition of the curable composition. Furthermore, it is thought that as the dispersed state (dispersed structure) of the inorganic spherical particles in the composite material according to the present embodiment, the dispersed state (dispersed structure) of the inorganic spherical particles in the curable composition immediately before being cured is substantially maintained as it is. In other words, although the dispersed state may be affected by polymerization shrinkage or the like at the time of curing, the influence thereof is small, and thus whether or not Conditions 1 and 2 described previously are satisfied is not affected.

<<Curable Composition>>

The curable composition according to the present embodiment contains the polymerizable monomer, the inorganic particles and the polymerization initiator, and the inorganic particles include one or more identical particle diameter spherical particle groups (G-PID) and the superfine particle group (G-SFP).

Although the curable composition according to the present embodiment is suitably used as a dental curable composition, in particular, a dental filling restorative material such as a photocurable composite resin, there is no limitation to the application, and the curable composition can be suitably used for other dental applications. Examples of the other applications include dental cement, a restorative material for abutment construction, and the like.

<Polymerizable Monomer and Inorganic Particles>

The polymerizable monomer is the same as the polymerizable monomer which is described as the raw material of the resin matrix in the composite material according to the present embodiment. G-PID and the inorganic spherical particles thereof and G-SFP and the inorganic particles thereof are the same as those which are described as the constituent components of the composite material according to the present embodiment.

As described previously, the average primary particle diameter of the inorganic spherical particles of G-PID is within a range of 100 to 1000 nm. Since the composite material easily obtains the short-range order structure described previously, G-PID is preferably one in which the inorganic spherical particles are coagulated and in which thus a coagulation particle is formed. For example, an average coagulation particle diameter of G-PID is preferably within a range of 5 to 200 μm, and more preferably within a range of 10 to 100 μm. The average coagulation particle diameter of G-PID can be calculated by a method which will be described later in the Examples.

The total content of G-PID in the curable composition is normally 10 to 1500 parts by mass with respect to 100 parts by mass of the polymerizable monomer. Since the obtained composite material has moderate transparency and the effect of developing a structural color is enhanced, the total content of G-PID in the curable composition is preferably 50 to 1500 parts by mass with respect to 100 parts by mass of the polymerizable monomer, and more preferably 100 to 1500 parts by mass. When a plurality of types of G-PID are included in the curable composition, with consideration given to the color tones of structural colors by each G-PID and a desired color tone in the composite material, the content of each G-PID is preferably set as necessary in the range into which the total content falls.

The content of G-SFP in the curable composition is determined as necessary with consideration given to the viscosity of the curable composition, the contrast ratio of the composite material, and the like. The content of G-SFP in the curable composition is normally 0.1 to 50 parts by mass with respect to 100 parts by mass of the polymerizable monomer, and preferably 0.2 to 30 parts by mass.

<Polymerization Initiator>

The polymerization initiator is not particularly limited as long as the polymerization initiator has the function of polymerizing and curing the polymerizable monomer. When a dental direct filling restoration application in which curing is often performed within an oral cavity is assumed, a chemical polymerization initiator and/or a photopolymerization initiator is preferably used, and since a mixing operation is not necessary, the photopolymerization initiator is more preferably used.

As the chemical polymerization initiator, a chemical polymerization initiator which is formed of two or more components and in which a polymerization initiation species (radical) is generated when these components make contact with each other can be used without particular limitation. Examples of the chemical polymerization initiator include chemical polymerization initiators which are formed by various combinations of organic peroxides/amines, organic peroxides/amines/organic sulfinic acids, organic peroxides/amines/arylborates, arylborates/acidic compounds, barbituric acid derivatives/copper compounds/halogen compounds, and the like. Among them, in terms of ease of handling, organic peroxides/amines are preferable.

Examples of the organic peroxides include hydroperoxides, peroxyketals, ketone peroxides, alkylsilyl peroxides, diacyl peroxides, peroxyesters, and the like, which are known.

Sulfinic acids such as benzenesulfinic acid, p-toluenesulfinic acid and salts thereof; barbituric acids such as 5-butylbarbituric acid; and the like may be mixed in the chemical polymerization initiator formed of organic peroxides/amines.

Examples of the polymerization initiator which can be used include benzoin alkyl ethers such as benzoin methyl ether, benzoin ethyl ether, and benzoin isopropyl ether; benzyl ketals such as benzyl dimethyl ketal and benzyl diethyl ketal; benzophenones such as benzophenone, 4,4'-dimethylbenzophenone, and 4-methacryloxybenzophenone; α-diketones such as diacetyl, 2,3-pentadionebenzyl, camphorquinone, 9,10-phenanthraquinone, and 9,10-anthraquinone; thioxanthone compounds such as 2,4-diethoxythioxanthone, 2-chlorothioxanthone, and methylthioxanthone; and bisacylphosphine oxides such as bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-propylphenylphosphine oxide, bis-(2,6-dichlorobenzoyl)-1-naphthylphosphine oxide, and bis(2,4,6-trimethylbenzoyl)-phenylphosphine oxide, and the like.

As the photopolymerization initiator, a reducing agent is often added, and examples thereof include tertiary amines such as 2-(dimethylamino)ethyl methacrylate, ethyl 4-dimethylaminobenzoate and N-methyldiethanolamine; aldehydes such as lauryl aldehyde, dimethylaminobenzaldehyde and terephthalic aldehyde; and sulfur-containing compounds such as 2-mercaptobenzoxazole, 1-decanethiol, thiosalicylic acid and thiobenzoic acid; and the like.

Furthermore, examples where a photoacid generator is added in addition to the photopolymerization initiator and the reducing agent described above are often seen. Examples of the photoacid generator as described above include a diaryliodonium salt-based compound, a sulfonium salt-based compound, a sulfonic acid ester compound, a halomethyl-substituted-S-triazine derivative, a pyridinium salt-based compound, and the like.

These polymerization initiators may be used singly, or two or more types thereof may be mixed so as to be used. Although as the amount of polymerization initiator mixed, an effective amount is preferably selected according to the purpose, 0.01 to 10 parts by mass of the polymerization initiator with respect to 100 parts by mass of the polymerizable monomer is normally used, and 0.1 to 5 parts by mass is more preferably used.

<Preferred Form in Curable Composition>

Preferably, in the curable composition according to the present embodiment, since the short-range order structure described above can be obtained more simply and reliably, at least part of one or more identical particle diameter spherical particle groups include one type of identical particle diameter spherical particle group and a resin whose refractive index at 25° C. is less than the refractive index of the inorganic spherical particles of the one type of identical particle diameter spherical particle group at 25° C., and are mixed as an organic-inorganic composite filler (that is, an organic-inorganic composite filler including only a single G-PID) which does not include a identical particle diameter spherical particle group other than the one type of the identical particle diameter spherical particle group.

Here, the organic-inorganic composite filler means a filler made of a powder that is formed with a complex in which an inorganic filler is dispersed in an (organic) resin matrix or a coagulated material in which the primary particles of an inorganic filler are bonded together with an (organic) resin.

In the preferred form described above, for example, when three types of G-PID having different average primary particle diameters, that is, $G\text{-}PID_1$, $G\text{-}PID_2$ and $G\text{-}PID_3$ are included, all or part of at least one type thereof is mixed as the "organic-inorganic composite filler including only a single G-PID". If all of $G\text{-}PID_1$ is mixed as the organic-inorganic composite filler including only $G\text{-}PID_1$ (composite filler 1) in the curable composition, within the composite filler 1, only $G\text{-}PID_1$ is included, and thus a short-range order structure for developing the structural color of $G\text{-}PID_1$ is realized, with the result that even in the composite material in which the curable composition is cured, the structural color of $G\text{-}PID_1$ is reliably developed. When $G\text{-}PID_1$ is mixed without being formed into a composite filler, since $G\text{-}PID_1$ is kneaded with $G\text{-}PID_2$ and $G\text{-}PID_3$ which are mixed simultaneously (without being formed into a composite), it is thought that the constituent particles of $G\text{-}PID_1$ and the constituent particles of $G\text{-}PID_3$ are somewhat substituted with each other, that thus the closest particles of the inorganic spherical particles of $G\text{-}PID_1$ are formed into the inorganic particles of $G\text{-}PID_3$ and that in a region where the inorganic spherical particles are the center, the short-range order structure is destroyed. By contrast, when all of $G\text{-}PID_1$ is mixed as the composite filler 1, the mutual substitution of the particles as described above does not occur, the short-range order structure is not destroyed, and thus it is possible to minimize the proportion of the inorganic spherical particles which do not involve the development of the structural color, with the result that even in the composite material after being cured, the structural color of $G\text{-}PID_1$ can be reliably developed. Likewise, $G\text{-}PID_2$ and/or $G\text{-}PID_3$ are mixed as an organic-inorganic composite filler including only $G\text{-}PID_2$ (composite filler 2) and/or an organic-inorganic composite filler including only $G\text{-}PID_3$ (composite filler 3), and thus the structural colors thereof can be reliably developed.

Since the effect described above can be expected and furthermore, the viscosity of the curable composition is easily adjusted, 10 to 90% of each G-PID is mixed as the "organic-inorganic composite filler including only a single G-PID", 20 to 80% thereof is preferably mixed, and 30 to 70% thereof is more preferably mixed.

When G-PID is mixed in a form other than the form of "organic-inorganic composite filler including only a single G-PID", though G-PID is generally mixed in the form of a powder (G-PID itself serving as the aggregate of the inorganic spherical particles), G-PID can be mixed as an organic-inorganic composite filler including a plurality of types of G-PID. A detailed description of the organic-inorganic composite filler including this case will be given below.

(Organic-Inorganic Composite Filler)

As described above, the organic-inorganic composite filler means a filler made of a powder that is formed with a complex in which an inorganic filler is dispersed in an (organic) resin matrix or a coagulated material in which the primary particles of an inorganic filler are bonded together with an (organic) resin.

In the organic-inorganic composite filler in the curable composition according to the present embodiment, as the inorganic filler, the inorganic spherical particles are used, and as the resin forming the (organic) resin matrix, the resin whose refractive index at 25° C. is less than the refractive index of the inorganic spherical particles at 25° C. is used. Although the resin described above is not particularly limited as long as the resin satisfies the condition as described above, the resin is preferably the cured product of the polymerizable monomer used when the resin matrix of the composite material is produced. Although here, the resin does not need to have exactly the same composition as the components of the polymerizable monomer in the curable composition, the resin whose refractive index at 25° C. is substantially equal to the refractive index of the polymerizable monomer at 25° C. is preferably used. When the refractive index of the resin described above at 25° C. is assumed to be $n_{(R)}$, and the refractive index of the inorganic spherical particles at 25° C. is assumed to be $n_{(F)}$, for any organic-inorganic composite filler, a relationship of $n_{(R)} < n_{(F)}$ needs to hold true. When the organic-inorganic composite filler includes inorganic spherical particles whose refractive index at 25° C. is different, the relationship described above needs to hold true for all the inorganic spherical particles. $\Delta n$ ($= n_{(F)} - n_{(R)}$), which is a difference between $n_{(F)}$ and $n_{(R)}$, is preferably 0.001 to 0.01, and more preferably 0.001 to 0.005.

The amount of inorganic spherical particles mixed in the organic-inorganic composite filler is preferably 30 to 95% by mass. When the amount thereof mixed in the organic-inorganic composite filler is equal to or greater than 30% by mass, the colored light of the cured product of the curable composition is satisfactorily developed, and mechanical strength can also be sufficiently enhanced. It is difficult to perform an operation of containing 95% or more by mass of the inorganic spherical particles in the organic-inorganic composite filler, and it is difficult to obtain a homogeneous mixture. The more preferred amount of inorganic spherical particles mixed in the organic-inorganic composite filler is 40 to 90% by mass.

The organic-inorganic composite filler can be produced according to a general production method in which predetermined amounts of individual components of the inorganic spherical particles, the polymerizable monomer, and the polymerization initiator are mixed together, and in which the mixture is polymerized by a method such as heating or light application and is thereafter pulverized. With the method as described above, it is possible to obtain the irregularly shaped organic-inorganic composite filler formed of a complex in which the inorganic spherical particles are dispersed in the resin matrix.

The organic-inorganic composite filler can also be produced by a method disclosed in PCT International Publication Nos. WO2011/115007 and WO2013/039169, that is, a method in which after coagulated particles formed of a coagulated material of inorganic spherical particles are immersed in a liquid composition including a polymerizable monomer, a polymerization initiator and an organic solvent, the organic solvent is removed, and in which the polymerizable monomer is polymerized and cured by a method such as heating or light application. With the method as described above, while a state where the primary particles of the inorganic spherical particles are coagulated is being substantially kept, a resin covers at least part of the surfaces of each of the primary particles, each of the primary particles are bonded to each other and thus it is possible to obtain a porous organic-inorganic composite filler having a large number of fine holes which communicate with the outside.

Although the average particle diameter of the organic-inorganic composite filler is not particularly limited, since the mechanical strength of the composite material and the operability of the curable composition are satisfactory, the average particle diameter is preferably 2 to 100 μm, more preferably 5 to 50 μm and further preferably 5 to 30 μm.

A pigment, a polymerization inhibitor, a fluorescent brightening agent, and the like can be added to the organic-inorganic composite filler as long as the effects thereof are not inhibited (in general, as long as 0.0001 to 5 parts by mass thereof with respect to 100 parts by mass of the organic-inorganic composite filler is added). The organic-inorganic composite filler may be surface-treated with a silane coupling agent or the like.

The amount of organic-inorganic composite filler mixed in the curable composition is preferably determined, with consideration given to the amount of identical particle diameter spherical particle group not being formed into the organic-inorganic composite filler mixed in the curable composition, by conversion from the amount of inorganic spherical particles included in the organic-inorganic composite filler such that the total amount of G-PID (that is, the total amount of inorganic spherical particles) falls into the range described above.

<Other Additives>

Other additives such as a polymerization inhibitor and a UV absorber can be mixed in the curable composition according to the present embodiment as long as the effects thereof are not inhibited.

The composite material obtained from the curable composition according to the present embodiment develops, as described above, a structural color without use of a coloring substance such as a pigment. Hence, a pigment which is likely to discolor as time passes does not need to be mixed in the curable composition according to the present embodiment. However, the mixing of a pigment itself is not necessarily denied, and a pigment may be mixed as long as the pigment does not prevent colored light caused by interference of a spherical filler. Specifically, about 0.0005 to 0.5 parts by mass of a pigment with respect to 100 parts by mass of the polymerizable monomer may be mixed, and about 0.001 to 0.3 parts by mass may be preferably mixed.

<<Method for Producing Curable Composition>>

A method for producing the curable composition according to the present embodiment is a method for producing the curable composition described above and according to the present embodiment, and includes a mixing step of mixing the polymerizable monomer, the inorganic particles, and the polymerization initiator. In the mixing step, necessary amounts of polymerizable monomer, inorganic particles, and polymerization initiator are respectively weighed and are mixed together. A method of weighing individual components and a method of mixing them here are not particularly limited. Since the mixed state of the curable composition is made uniform for a short period of time, and scale-up production is easily performed, mixing using a kneading device such as a planetary motion-type stirrer is preferably performed.

In the mixing step, the mixing needs to be performed by adopting mixing conditions under which on a mixture obtained in this step, the dispersed state of the inorganic particles in the cured product obtained by curing the mixture satisfies conditions (I) and (II) described previously. Here, conditions (I) and (II) which need to be satisfied by the cured product of the mixture are conditions which are obtained by replacing the term "composite material" in conditions 1 and 2 that need to be satisfied by the composite material with the term "cured product of the mixture", and thus the detailed description thereof will be omitted.

As a method of determining the mixing conditions adopted in the mixing step, the method of (a) or (b) below is preferable.

(a) The method in which, previously, on a curable composition having the same or substantially same composition as the actually produced curable composition, a plurality of mixing conditions are changed and the mixing is performed, the radial distribution function g(r) in the cured product of the mixture obtained when the mixing is performed under each of the mixing conditions is checked so as to determine the mixing conditions which satisfy conditions (I) and (II), and the same mixing conditions as the determined mixing conditions are adopted.

(b) The method in which part of the mixture obtained partway through and/or after completion of the mixing step is sampled, whether or not the dispersed state of the inorganic particles in the cured product of the sampled mixture satisfies conditions (I) and (II) is checked and the mixing is continued until these conditions are satisfied.

Here, the satisfaction of condition (I) means that the inorganic spherical particles are dispersed while holding constant short-range order, and the satisfaction of condition (II) means that the inorganic spherical particles are dispersed in a state where long-range order is random while short-range order is being maintained (which is not a completely random state where short-range order collapses and which is a state where fine domains having short-range order are randomly dispersed). Preferably, in order to easily satisfy these conditions, in the mixing step, the inorganic spherical particles are mixed as an organic-inorganic composite filler having a particle diameter of 5 to 50 μm and preferably a particle diameter of 5 to 30 μm, or are mixed as coagulated particles having a particle diameter of 5 to 200 μm and preferably a particle diameter of 10 to 100 μm. When air bubbles are mixed during the mixing, not only it is difficult to satisfy the conditions described above, but also a defect in the composite material is caused, and thus it is preferable to perform, for example, defoaming treatment such that at least air bubbles are not left after the mixing. Since air bubbles can be removed from within a composition having a high viscosity for a short period of time, as a defoaming method, a method of performing defoaming under reduced pressure is preferably adopted. Furthermore, the mixing is preferably performed such that the total amount of identical particle diameter spherical particle group is 50 to 1500 parts by mass with respect to 100 parts by mass of the polymerizable monomer and preferably 100 to 1500 parts by mass.

Although when the inorganic spherical particles are mixed with attention being given to such points, in principle, the conditions described above are satisfied by performing sufficient stirring, stirring may be insufficient from the viewpoint that the conditions described above are satisfied even when it is visually determined that a uniform state is achieved, with the result that it is difficult to determine the end point thereof. Hence, the mixing step is preferably performed after the end point is determined or while the end point is being determined by the method of (a) or (b) described above.

When the method of (a) described above is adopted, for example, the mixing conditions can be determined as follows. As a mixing method, a kneading method using a planetary motion-type stirrer (planetary mixer) is first adopted, a device to be actually used is used, individual raw materials are prepared such that the same composition as the curable composition to be actually produced is provided and simulated kneading is performed a plurality of times while various types of conditions such as a rotation speed, a kneading time and a defoaming condition after the kneading are respectively being changed. Then, the radial distribution function g(r) is checked for the cured product of a mixture obtained in each round of the simulated kneading, and thus the mixing conditions for providing the cured product which satisfies conditions (I) and (II) described above are determined.

When the mixing conditions are determined by the method of (a) described above, predetermined kneading conditions are only set so as to be able to reliably produce an intended curable composition, and thus when the same curable composition (of the same composition and the same amount) is produced, it is not necessary to change conditions each time, with the result that the efficiency of the operation can be enhanced in that excessive kneading (unnecessary extended kneading) can be prevented.

On the other hand, when the method of (b) described above is adopted, for example, the mixing conditions can be determined as shown in the flow diagram of FIG. 1. The polymerizable monomer, the inorganic particles, and the polymerization initiator, which are the raw materials, are first put into the kneading device (step S10) so as to be kneaded (step S11). Then, part of a mixture obtained partway through and/or after completion of the mixing is sampled, and the radial distribution function g(r) is checked for the cured product of the sampled mixture (step S12). Then, whether or not the dispersed state of the inorganic particles in the cured product satisfies conditions (I) and (II), that is, whether or not the dispersed state is sufficient is determined (step S13), and when the dispersed state is sufficient, all the amount is collected (step S14) whereas when the dispersed state is insufficient, the kneading is continued.

The method of (b) described above can be said to be a desirable method especially when a curable composition in which the composition and the amount are changed each time is produced.

EXAMPLES

Although the present invention will be more specifically described below using Examples, the present invention is not limited to these Examples.

The composite materials of the Examples and Comparative Examples were all obtained by curing curable compositions containing a polymerizable monomer, inorganic particles, and a polymerization initiator. Individual components which were used in the curable compositions of Examples and Comparative Examples will first be described.

1. Polymerizable Monomer

As the polymerizable monomer, M1 and M2, which were the polymerizable monomer mixtures of the compositions shown in table 1, were used. Symbols in the polymerizable monomer column of the table represent compounds below respectively, and numbers within parentheses indicate parts by mass which were used.

UDMA: 1,6-bis (methacrylethyloxycarbonylamino) trimethylhexane

3G: triethylene glycol dimethacrylate bis-GMA: 2,2-bis [(3-methacryloyloxy-2-hydroxypropyloxy) phenyl] propane The viscosities of M1 and M2 were measured with an E-type viscometer (made by Tokyo Keiki Co., Ltd., "VISCONIC ELD") in a constant temperature chamber of 25° C.

The refractive index before curing (M1 or M2) and the refractive index after curing (cured product) were measured with an Abbe refractometer (made by Atago Co., Ltd.) in the constant temperature chamber of 25° C. A cured product sample was produced as follows: 0.2% by mass of camphorquinone (CQ), 0.3% by mass of ethyl p-N,N-dimethylaminobenzoate (DMBE) and 0.15% by mass of hydroquinone monomethyl ether (HQME) were added as the polymerization initiator to 100 parts by mass of M1 or M2 and were uniformly mixed, the resulting mixture was put into a mold having a through-hole of 7 mm$\phi$×0.5 mm, polyester films were pressed on both sides, then curing was performed by light application for 30 seconds with a halogen-type dental light irradiator having a light intensity of 500 mW/cm$^2$ (made by Sybron Dental Specialties Inc., "Demetron LC") and thereafter the cured product sample was taken out of the mold. When the cured product sample was set in the Abbe refractometer, in order for the cured product sample and a measurement surface to be brought into intimate contact with each other, a solvent (bromonaphthalene) which did not dissolve the sample and whose refractive index was higher than that of the sample was dropped onto the sample.

TABLE 1

| Monomer name | Polymerizable monomer | Polymerizable monomer viscosity [mPa · s] | Refractive index Before curing | Refractive index After curing |
|---|---|---|---|---|
| M1 | UDMA (60)/3G (40) | 150.14 | 1.474 | 1.509 |
| M2 | bis-GMA (60)/3G (40) | 755.65 | 1.515 | 1.546 |

2. Inorganic Particles 2-1. Identical Particle Diameter Spherical Particle Group (G-PID)

As G-PID, G-PID1 to G-PID11 shown in table 2 were used. These identical particle diameter spherical particle groups were prepared according to a method (so-called sol-gel method) disclosed in Japanese Unexamined Patent Application Publications Nos. 58-110414 and 58-156524 and the like. Specifically, a mixed solution which included a hydrolyzable organosilicon compound (such as tetraethyl silicate) and a hydrolyzable organic titanium group metal compound (such as tetrabutylzirconate or tetrabutyltitanate) such that compositions shown in the composition column of table 2 were provided was added into an ammonia alcohol solution (for example, methanol, ethanol, isopropyl alcohol or isobutyl alcohol) into which ammonia water was introduced and hydrolysis was performed to precipitate a reaction product. Then, the resulting precipitate was separated, was thereafter dried and was calcined after being pulverized as necessary, with the result that a calcined product was obtained. Then, 4 parts by mass of γ-methacryloyloxypropyltrimethoxysilane and 3 parts by mass of n-propylamine with respect to 100 parts by mass of the obtained calcined product were stirred and mixed in 500 parts by mass of methylene chloride, methylene chloride was removed with an evaporator and thereafter heat-drying was performed at 90° C., with the result that surface-treated identical particle diameter spherical particle groups were obtained.

The average primary particle diameter, the average coagulation particle diameter, the existence ratio of average particle diameter particles, the average uniformity and the refractive index in table 2 were measured as follows.

(1) Average Primary Particle Diameter

A photograph of a powder was shot with a scanning electron microscope (made by Philips N.V., "XL-30S") at a magnification of 5000 to 100000 times, the shot image was processed with image analysis software (made by Asahi Kasei Engineering Corp., "IP-1000PC"), the number (30 or more particles) and the primary particle diameter (maximum diameter) of particles observed within a unit field of view of the photograph were measured and the average primary particle diameter was calculated by a formula below based on the measured values.

$$\bar{x} = \frac{\sum_{i=1}^{n} x_i}{n} \text{ (Number average)}$$

($n$: number of particles, $x_i$: primary particle diameter (maximum diameter) of $i$-th particle)

(2) Average Coagulation Particle Diameter 0.1 g of G-PID was dispersed in 10 mL of ethanol, and was sufficiently shaken manually. With a particle size distribution meter (made by Beckman Coulter, Inc., "LS230") using a laser diffraction-scattering method, the median diameter of volume statistics is determined in an optical model "Franhofer", and this was used as the average coagulation particle diameter of G-PID.

(3) Existence Ratio of Average Particle Diameter Particles

[ratio (%) of the number of particles present within a range of plus or minus 5% of the average primary particle diameter in a number-based particle size distribution to the number of all particles]

Among all particles (30 or more particles) within a unit field of view of the photograph shot in (1) described above, the number of particles having a primary particle diameter (maximum diameter) outside a particle diameter range of plus or minus 5% of the average primary particle diameter determined in (1) described above was measured, the value thereof was subtracted from the number of all particles, thus the number of particles within the particle diameter range of plus or minus 5% of the average primary particle diameter within the unit field of view of the photograph was determined and the existence ratio of average particle diameter particles was calculated according to a formula below.

Existence ratio of average particle diameter particles (%)=[(number of particles within particle diameter range of plus or minus 5% of average primary particle diameter within unit field of view of scanning electron microscope photograph)/(number of all particles within unit field of view of scanning electron microscope photograph)]×100

(4) Average Uniformity

A photograph of the powder was shot with the scanning electron microscope, the number (n: 30 or more) of particles of the same particle diameter spherical particle group (G-PID) observed within a unit field of view of the photograph, the major diameter (Li), which was the maximum diameter of the particle, and the minor diameter (Bi), which was a diameter in a direction orthogonal to the major diameter, were determined, and thus the average uniformity was calculated by a formula below.

$$\text{Average uniformity} = \frac{\sum_{i=1}^{n} Bi/Li}{n}$$

(5) Refractive Index

The refractive index was measured with the Abbe refractometer (made by Atago Co., Ltd.) by a liquid immersion method. Specifically, in the constant temperature chamber of 25° C., within a sample bottle of 100 mL, the identical particle diameter spherical particle group (G-PID) was dispersed in 50 mL of anhydrous toluene. While this dispersion liquid was being stirred with a stirrer, 1-bromotoluene was dropped little by little, the refractive index of the dispersion liquid when the dispersion liquid was the most transparent was measured, and the obtained value was used as the refractive index of the identical particle diameter spherical particle group (G-PID).

TABLE 2

|  | Composition and shape of filler | | Average primary particle diameter (nm) | Average coagulation particle diameter (μm) | Refractive index | Existence ratio of average particle diameter particles (%) | Average uniformity |
|---|---|---|---|---|---|---|---|
|  | Composition (mol %) | Shape | | | | | |
| G-PID1 | SiO$_2$/ZrO$_2$/Na$_2$O = 89.8/9.0/1.2 | spherical | 80 | 24.2 | 1.515 | 91 | 0.98 |
| G-PID2 | SiO$_2$/ZrO$_2$/Na$_2$O = 89.8/9.0/1.2 | spherical | 200 | 61.7 | 1.515 | 93 | 0.97 |
| G-PID3 | SiO$_2$/ZrO$_2$/Na$_2$O = 89.8/9.0/1.2 | spherical | 238 | 44.5 | 1.515 | 96 | 0.95 |
| G-PID4 | SiO$_2$/ZrO$_2$/Na$_2$O = 89.8/9.0/1.2 | spherical | 250 | 30.2 | 1.515 | 95 | 0.92 |
| G-PID5 | SiO$_2$/ZrO$_2$/Na$_2$O = 89.8/9.0/1.2 | spherical | 262 | 27.6 | 1.515 | 95 | 0.94 |
| G-PID6 | SiO$_2$/ZrO$_2$/Na$_2$O = 89.8/9.0/1.2 | spherical | 275 | 50.8 | 1.515 | 92 | 0.93 |

TABLE 2-continued

|  | Composition and shape of filler | | Average primary particle diameter (nm) | Average coagulation particle diameter (μm) | Refractive index | Existence ratio of average particle diameter particles (%) | Average uniformity |
|---|---|---|---|---|---|---|---|
|  | Composition (mol %) | Shape |  |  |  |  |  |
| G-PID7 | $SiO_2/ZrO_2/Na_2O$ = 89.8/9.0/1.2 | spherical | 280 | 32.6 | 1.515 | 94 | 0.93 |
| G-PID8 | $SiO_2/ZrO_2/Na_2O$ = 89.8/9.0/1.2 | spherical | 295 | 107.3 | 1.515 | 92 | 0.94 |
| G-PID9 | $SiO_2/ZrO_2/Na_2O$ = 89.8/9.0/1.2 | spherical | 331 | 55.2 | 1.515 | 92 | 0.92 |
| G-PID10 | $SiO_2/ZrO_2/Na_2O$ = 89.8/9.0/1.2 | spherical | 367 | 33.5 | 1.515 | 90 | 0.94 |
| G-PID11 | $SiO_2/ZrO_2/Na_2O$ = 89.8/9.0/1.2 | spherical | 400 | 12.7 | 1.515 | 91 | 0.94 |
| F1 | $SiO_2/ZrO_2/Na_2O$ = 89.8/9.0/1.2 | irregular shape | 500 | — | 1.515 | 50 | — |

2-2. Organic-Inorganic Composite Filler (CF1)

100 g of the same particle diameter spherical particle group (G-PID5) shown in table 2 was added to 200 g of water, and a water dispersion liquid thereof was obtained with a circulation-type pulverizer SC mill (made by Nippon Coke & Engineering Co., Ltd.).

On the other hand, 4 g (0.016 mol) of γ-methacryloyloxy-propyltrimethoxysilane and 0.003 g of acetic acid were added to 80 g of water, and they were stirred for 1 hour and 30 minutes, with the result that a uniform solution of pH 4 was obtained. This solution was added to the water dispersion liquid described above, and they were mixed until the dispersion liquid became uniform. Thereafter, while the dispersion liquid was being mixed lightly, the dispersion liquid was supplied onto a disc rotating at high speed and was granulated by a spray drying method. Spray drying was performed with a spray dryer TSR-2W (made by Sakamoto Giken Co., Ltd.) which included a rotating disc and which sprayed by centrifugal force. The rotation speed of the disc was 10000 rpm, and the temperature of air in a dry atmosphere was 200° C. Thereafter, a powder obtained by being granulated by spray drying was dried in a vacuum at 60° C. for 18 hours, and 73 g of a substantially spherical coagulated material was obtained.

Then, 50 g of the coagulated material described above was immersed in a polymerizable monomer solution (containing 36 parts by mass of the polymerizable monomer with respect to 100 parts by mass of an organic solvent) obtained by mixing 10 g of the polymerizable monomer mixture M1, 0.025 g of azobisisobutyronitrile (AIBN) serving as a thermal polymerization initiator and furthermore 5.0 g of methanol serving as the organic solvent. The resulting mixture was sufficiently stirred, was confirmed to be brought into a slurry state and was thereafter left to stand for one hour.

The mixture described above was transferred into a rotary evaporator. In a stirred state, the mixture was dried for one hour under conditions in which the degree of pressure reduction was 10 hPa and in which a heating condition was 40° C. (a warm water bath was used), with the result that the organic solvent was removed. When the organic solvent was removed, a powder having high fluidity was obtained. While the obtained powder was being stirred in the rotary evaporator, the powder was heated for one hour under conditions in which the degree of pressure reduction was 10 hPa and in which a heating condition was 100° C. (an oil bath was used), and thus the polymerizable monomer in the powder was polymerized and cured. With this operation, 45 g of the substantially spherical organic-inorganic composite filler (CF1) in which the surface of a spherical coagulated material was coated with an organic polymer was obtained. The average particle diameter of the organic-inorganic composite filler was 33 μm.

2-3. Superfine Particles (G-SFP)

As G-SFP, REOLOSIL QS102 (average primary particle diameter of 30 nm, made by Tokuyama Corporation) was used.

2-4. Irregularly Shaped Inorganic Particles

Irregularly shaped inorganic particles F1 shown in table 2 were used. The irregularly shaped inorganic particles F1 were prepared according to a method disclosed in Japanese Unexamined Patent Application Publications Nos. 2-132102 and 3-197311 and the like as follows: an alkoxysilane compound was dissolved in an organic solvent, water was added thereto so as to perform partial hydrolysis, thereafter an alkoxide of another metal and an alkali metal compound which were formed into a composite were further added so as to perform hydrolysis and to thereby generate a gel-like material and then the gel-like material was dried, was thereafter pulverized as necessary, and was calcined. The average primary particle diameter (which means, for the irregularly shaped inorganic particles, the average particle diameter of pulverized particles), the existence ratio of average particle diameter particles and the refractive index were measured as in G-PID.

3. Polymerization Initiator

As the polymerization initiator, a polymerization initiator formed by combination of camphorquinone (CQ), ethyl p-N,N-dimethylaminobenzoate (DMBE), and hydroquinone monomethyl ether (HQME) was used.

Reference Example 1

The curable composition of Reference Example 1 was produced according to the flow diagram of FIG. 1. Specifically, 4.8 g of CQ, 16.0 g of DMBE and 2.4 g of HQME were added to 1600 g of the polymerizable monomer mixture M1, they were mixed together and thus a uniform polymerizable monomer composition was prepared. Then, 6400 g of G-PID4 was weighed, the polymerizable monomer composition described above was gradually added under red light and they were kneaded by use of a planetary motion-type stirrer planetary mixer with a stirring container having a capacity of 15 L (made by INOUE MFG., INC.) at the rotation speed of a stirring blade of 7 to 10 rpm for 2 hours. The kneading was temporarily stopped, and 5.0 g of the mixture was sampled. On this sample, decompression defoaming treatment was performed at a pressure of 1000 Pa for 5 minutes, and the sample was cured by light application for 30 seconds with a visible light irradiator (made by Tokuyama Corporation, Power Light). When the radial distribution function g(r) was checked for the obtained cured product in the same method as in Example 1 which will be described later, in a position ($r_1/r_0$ was 0.88) where the closest particle-to-particle distance $r_1$ was 0.88 times a particle diameter $r_0$, the first local maximum peak of the radial distribution function g(r) was observed and the local minimum value of the radial distribution function g(r) between the closest particle-to-particle distance $r_1$ and the second closest particle-to-particle distance $r_2$ was 0.32, with the result that conditions 1 and 2 of the radial distribution function were not satisfied. Hence, when the kneading was further performed for one hour under the same conditions, then sampling was performed and the radial distribution function g(r) of the cured product was checked, in a position ($r_1/r_0$ was 1.03) where the closest particle-to-particle distance $r_1$ was 1.03 times the particle diameter $r_0$, the first local maximum peak of the radial distribution function g(r) was observed and the local minimum value of the radial distribution function g(r) between the closest particle-to-particle distance $r_1$ and the second closest particle-to-particle distance $r_2$ was 0.60, with the result that it was confirmed that conditions 1 and 2 of the radial distribution function were satisfied. When as a reproducibility test, a kneading time was set to 3 hours from the beginning, the kneading was performed with the planetary mixer, all the amount was taken out and the radial distribution function g(r) of the cured product was checked, it was confirmed that conditions 1 and 2 of the radial distribution function were satisfied. In Reference Example 1, uniform compositions which satisfied conditions 1 and 2 of the radial distribution function were obtained at a ratio of 10 out of 10 tests with high reducibility.

Example 1

Figure 2A:
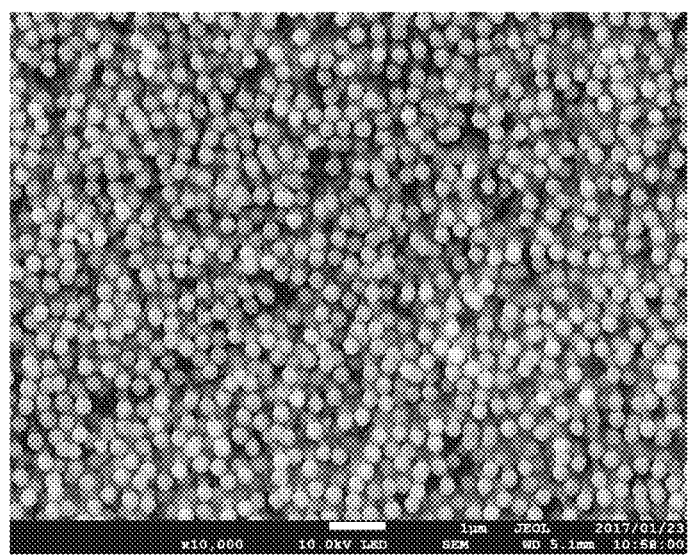
FIG. 2A is a diagram showing an example of a scanning electron microscope image in an observation plane of the composite material of Example 1.
Figure 2B:
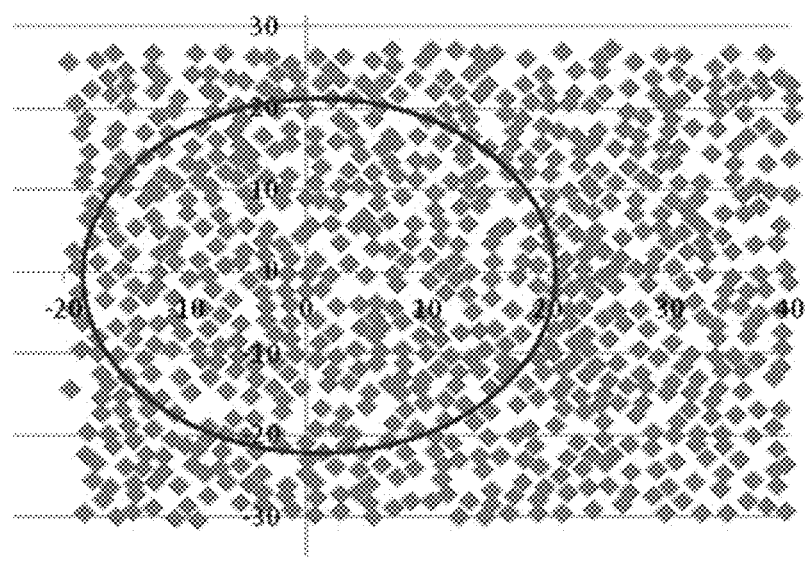
FIG. 2B is a diagram showing an example of coordinate data obtained from the scanning electron microscope image of FIG. 2A.
Figure 3:
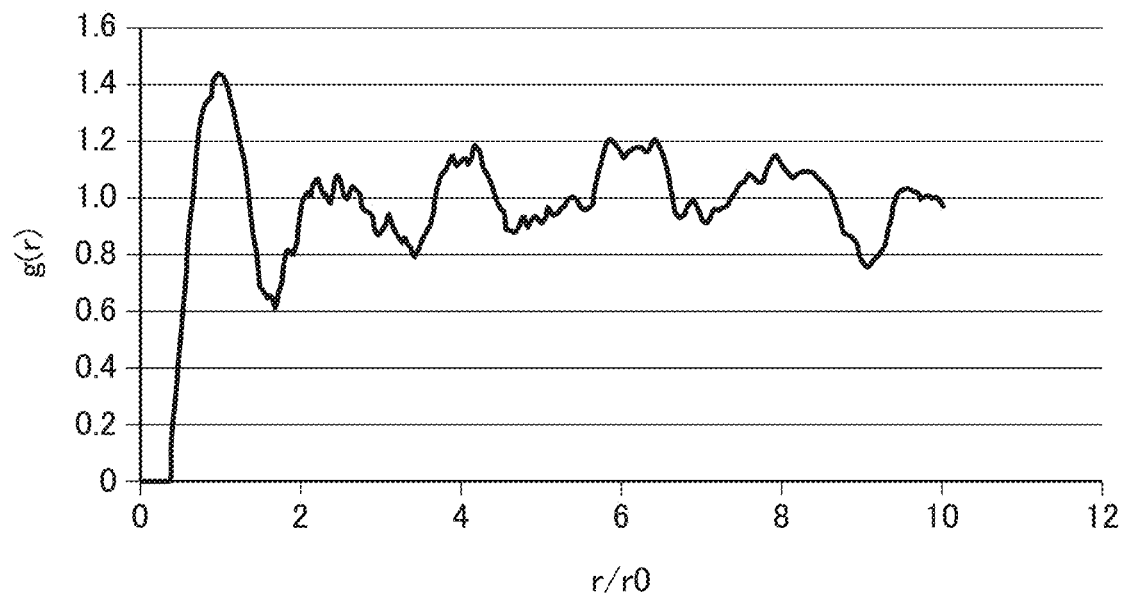
FIG. 3 is a diagram showing a radial distribution function graph for g(r) calculated based on a parameter determined from the coordinate data of FIG. 2B.

0.3 parts by mass of CQ, 1.0 part by mass of DMBE and 0.15 parts by mass of HQME were added to 100 parts by mass of the polymerizable monomer mixture M1, they were mixed together, and thus a uniform polymerizable monomer composition was prepared. Then, 400 parts by mass of G-PID4 and 0.5 parts by mass of a superfine particle group (G-SFP) were weighed, the polymerizable monomer composition described above was gradually added under red light and they were sufficiently kneaded by use of a kneader planetary mixer (made by INOUE MFG., INC.) so as to form into a uniform curable paste. Furthermore, the paste was defoamed under reduced pressure, and thus air bubbles were removed, with the result that a curable composition was produced. On the cured product (composite material) of the obtained curable composition, (1) the visual evaluation of colored light, (2) the measurement of the wavelength of the colored light, (3) the evaluation of color tone compatibility with a colorimeter, (4) the visual evaluation of color tone compatibility and (5) the evaluation of the radial distribution function of inorganic spherical particles were performed. The composition (in a matrix column, a polymerizable monomer mixture providing a resin for forming a matrix is described) of the cured product (composite material) and the results of the evaluations are shown in tables 3 to 5. An example of a scanning electron microscope image in an observation plane of the cured product (composite material) of Example 1 is shown in FIG. 2A, an example of coordinate data obtained from the scanning electron microscope image is shown in FIG. 2B and a radial distribution function graph on g(r) calculated based on a parameter determined from the coordinate data is shown in FIG. 3. In Example 1, uniform compositions which satisfied conditions 1 and 2 of the radial distribution function were obtained at a ratio of 10 out of 10 tests with high reducibility. The evaluations and measurements described above were performed by methods which will be described below.

(1) Visual Evaluation of Colored Light

The curable composition (paste) was put into a mold having a through-hole of 7 mmϕ×1 mm, and polyester films were pressed on both sides. Curing was performed by light application for 30 seconds on both sides with the visible light irradiator (made by Tokuyama Corporation, Power Light), and thereafter an evaluation sample was produced by being taken out of the mold. The obtained evaluation sample was placed on the adhesive surface of an about 10 mm square black tape (carbon tape), and the color tone of colored light was visually checked.

(2) Wavelength of Colored Light

On an evaluation sample produced in the same manner as in (1) described above, a spectral reflectivity was measured in a black background and in a white background with a color difference meter (made by Tokyo Denshoku Co., Ltd., "TC-1800MKII"), and the local maximum point of the reflectivity in the black background was assumed to be the wavelength of the colored light.

(3) Evaluation of Color Tone Compatibility with Colorimeter

A hard resin tooth in which a cavity of class I (diameter of 4 mm and a depth of 2 mm) was reproduced in the center portion of the occlusal surface of lower right number 6 was used, the curable composition (paste) described above was filled in a lost portion, curing and polishing were performed and thus simulated restoration was performed. The color tone compatibility after the simulated restoration was evaluated with a two-dimensional colorimeter (made by PaPaLab Co., Ltd., "RC-500"). As the hard resin tooth, a hard resin tooth of high chroma (corresponding to A4) and a hard resin tooth of low chroma (corresponding to A1) which were in the class of A system (reddish brown) in the shade guide ("VITA Classical", made by Vita Zahnfabrik H. Rauter GmbH & Co. KG) and a hard resin tooth of high chroma (corresponding to B4) and a hard resin tooth of low chroma (corresponding to B1) which were in the class of B system (reddish yellow) in the shade guide ("VITA Classical", made by Vita Zahnfabrik H. Rauter GmbH & Co. KG), were used. The hard resin tooth was set in the two-dimensional colorimeter, the hard resin tooth was shot, image analysis software (made by PaPaLab Co., Ltd., "RC Series Image Viewer") was used to process the shot image and a color difference ($\Delta E^*$ in CLELab) between the colorimetric values of the restored portion and the non-restored portion of the hard resin tooth was determined, with the result that the evaluation of the color tone compatibility was performed.

$$\Delta E^* = \{(\Delta L^*)^2 + (\Delta a^*)^2 + (\Delta b^*)^2\}^{1/2}$$

$$\Delta L^* = L1^* - L2^*$$

$$\Delta a^* = a1^* - a2^*$$

$$\Delta b^* = b1^* - b2^*$$

L1*: lightness index of restored portion of hard resin tooth, a1*, b1*: chroma index of restored portion of hard resin tooth, L2*: lightness index of non-restored portion of hard resin tooth, a2*, b2*: chroma index of non-restored portion of hard resin tooth and ΔE*: color tone variation amount (4) Visual Evaluation of Color Tone Compatibility The simulated restoration was performed in the same manner as in (3) described above, and color tone compatibility after the restoration was visually checked. The criteria are shown below.

—Criteria—

5: Color tone of restored product was indistinguishable from hard resin tooth
4: Color tone of restored product had good compatibility with hard resin tooth
3: Color tone of restored product was similar to hard resin tooth
2: Color tone of restored product was similar to hard resin tooth but was not satisfactorily compatible therewith
1: Color tone of restored product was not compatible with hard resin tooth (5) Evaluation of Radial Distribution Function of Inorganic Spherical Particles The curable composition (paste) was put into a mold having a through-hole of 5 mmφ×10 mm, and polyester films were pressed on both sides. Curing was performed by light application for 30 seconds on both sides with the visible light irradiator (made by Tokuyama Corporation, Power Light), and thereafter the cured product (composite material) of the curable composition (paste) was obtained by being taken out of the mold. The dispersed state of spherical particles in the cured product was observed with the scanning electron microscope (made by Philips N.V., "XL-30S"), the radial distribution function was determined and thus the evaluation was performed. Specifically, on the cured product, cross section milling was performed with an ion milling device (made by Hitachi, Ltd., "IM4000") under conditions of 2 kV and 20 minutes, and thus an observation plane was formed. For the observation plane, with the scanning electron microscope, a microscope image of a region which contained 1000 spherical particles within the plane was acquired, and the coordinates of the spherical particles within the region were determined on the obtained scanning electron microscope image with the image analysis software ("Simple Digitizer ver. 3.2" free software). One set of coordinates of an arbitrary spherical particle were selected from obtained coordinate data, with the selected spherical particle being the center, a circle in which at least 200 or more spherical particles were included and in which a distance r was the radius was drawn and the number of spherical particles included within the circle was determined, with the result that the average particle density $<\rho>$ (unit: pieces/cm$^2$) was calculated. dr was a value of about $r_0/100$ to $r_0/10$ ($r_0$ indicating the average particle diameter of the spherical particles), and the number dn of particles included within a region between a circle of a distance r from the spherical particle in the center and a circle of a distance r+dr and the area da of the region were determined. The values of $<\rho>$, do and da determined as described above were used, and thus the following formula (1) was calculated, with the result that the radial distribution function g(r) was determined.

$$g(r)=\{1/<\rho>\}\times\{dn/da\} \quad (1)$$

Then, a radial distribution function graph indicating a relationship between the radial distribution function and $r/r_0$ (r represented an arbitrary distance from the center of the circle and $r_0$ represented the average particle diameter of the spherical particles) was produced. Then, on conditions 1 and 2 of the radial distribution function, evaluations were performed with "Y" indicating the satisfaction of the condition and "N" indicating the dissatisfaction of the condition.

TABLE 3

| | Resin matrix | Identical particle diameter spherical particle group | superfine particle group | Refractive index difference* | Colored light visual evaluation | Colored light wavelength (nm) Black background | Colored light wavelength (nm) White background | Radial distribution function Condition 1 | Radial distribution function Condition 2 |
|---|---|---|---|---|---|---|---|---|---|
| Example 1 | M1 (100) | G-PID4 (400) | G-SFP (0.5) | 0.006 | yellow | 607 | no local maximum | Y | Y |
| Example 2 | M1 (100) | G-PID5(200)/ G-PID8(200) | G-SFP (1) | 0.006 | red | 695 | no local maximum | Y | Y |
| Example 3 | M1 (100) | G-PID4(200)/ G-PID7(100)/ G-PID9(100)/ G-PID10(100)/ G-PID11(100) | G-SFP (1) | 0.006 | red | 756 | no local maximum | Y | Y |
| Example 4 | M1 (100) | CF1(300)/ G-PID5(100) | G-SFP (1) | 0.006 | red | 720 | no local maximum | Y | Y |
| Comparative Example 1 | M2 (100) | G-PID4(400) | G-SFP (0.5) | −0.031 | blue | 481 | no local maximum | — | — |
| Comparative Example 2 | M1 (100) | G-PID2(400) | G-SFP (0.5) | 0.006 | deep blue | 430 | no local maximum | Y | N |
| Comparative Example 3 | M1 (100) | G-PID1(400) | G-SFP (0.5) | 0.006 | none | 405 | no local maximum | — | — |
| Comparative Example 4 | M1 (100) | F1(400) | G-SFP (0.5) | 0.006 | none | no local maximum | no local maximum | — | — |
| Comparative Example 5 | M1 (100) | G-PID3(100)/ G-PID4(200)/ G-PID5(200)/ G-PID6(100) | G-SFP (1) | 0.006 | none | no local maximum | no local maximum | — | — |

*refractive index of identical particle diameter spherical particle group (G-PID) − refractive index of polymer of resin matrix

TABLE 4

A system (reddish blown) color tone compatibility

| | Low chroma | | High chroma | |
|---|---|---|---|---|
| | Visual evaluation | ΔE* | Visual evaluation | ΔE* |
| Example 1 | 4 | 0.82 | 4 | 0.85 |
| Example 2 | 5 | 0.18 | 5 | 0.25 |
| Example 3 | 5 | 0.20 | 4 | 0.85 |
| Example 4 | 5 | 0.29 | 5 | 0.28 |
| Comparative Example 1 | 2 | 3.67 | 2 | 3.89 |
| Comparative Example 2 | 1 | 8.53 | 1 | 8.37 |
| Comparative Example 3 | 1 | 4.87 | 1 | 4.93 |
| Comparative Example 4 | 2 | 3.99 | 1 | 4.71 |
| Comparative Example 5 | 2 | 3.98 | 2 | 3.89 |

TABLE 5

B system (reddish yellow) color tone compatibility

| | Low chroma | | High chroma | |
|---|---|---|---|---|
| | Visual evaluation | ΔE* | Visual evaluation | ΔE* |
| Example 1 | 5 | 0.32 | 5 | 0.20 |
| Example 2 | 5 | 0.34 | 4 | 0.95 |
| Example 3 | 5 | 0.33 | 4 | 0.88 |
| Example 4 | 5 | 0.31 | 5 | 0.35 |
| Comparative Example 1 | 1 | 4.66 | 1 | 4.85 |
| Comparative Example 2 | 1 | 7.86 | 1 | 7.94 |
| Comparative Example 3 | 1 | 4.88 | 1 | 4.91 |
| Comparative Example 4 | 2 | 3.98 | 1 | 4.81 |
| Comparative Example 5 | 2 | 3.92 | 2 | 3.79 |

Examples 2 to 4

Figure 4:
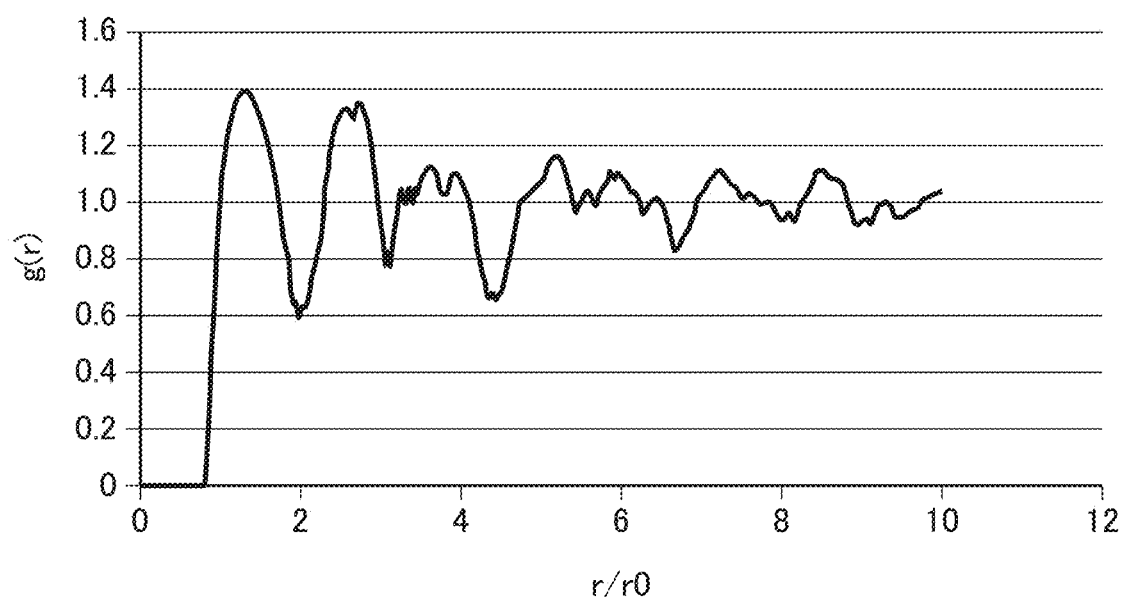
FIG. 4 is a diagram showing a radial distribution function graph for the composite material of Example 2.
Figure 5:
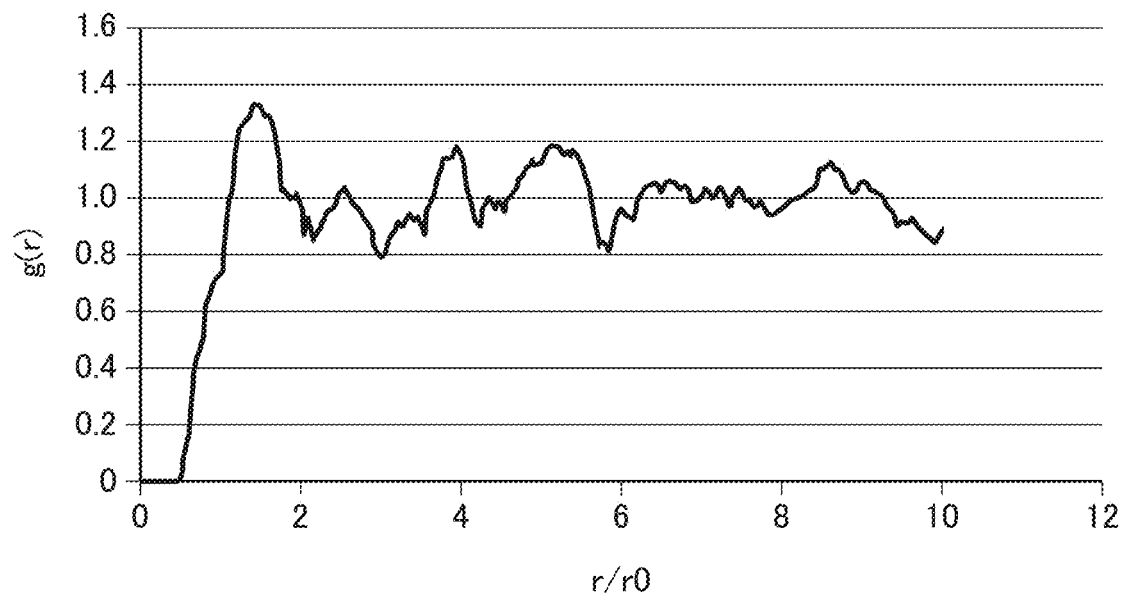
FIG. 5 is a diagram showing a radial distribution function graph for the composite material of Example 3.
Figure 6:
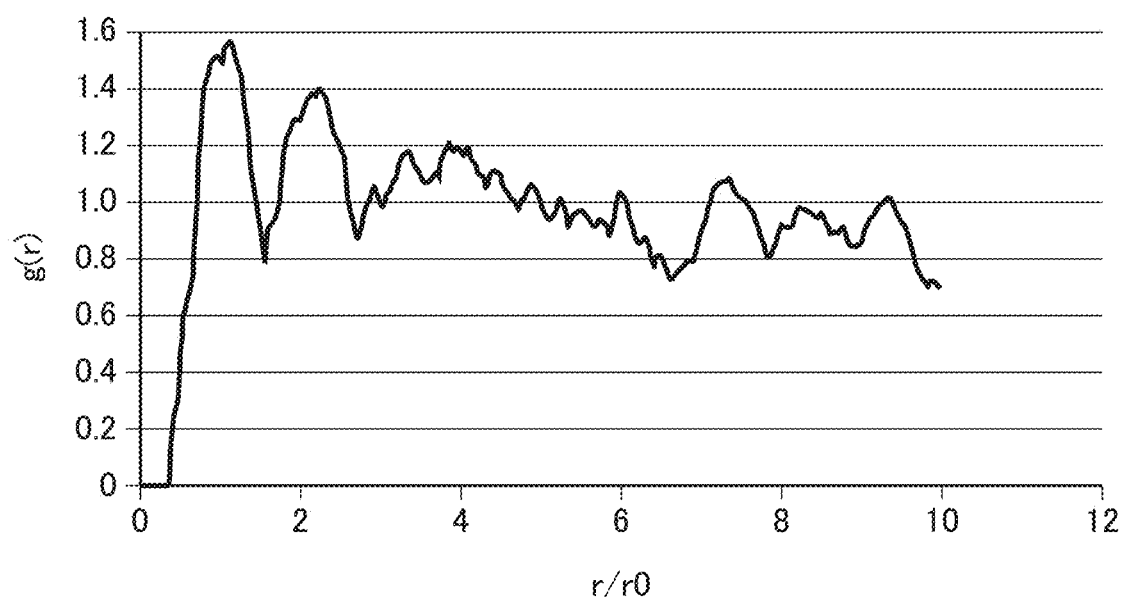
FIG. 6 is a diagram showing a radial distribution function graph for the composite material of Example 4.

Cured products (composite materials) were obtained in the same manner as in Example 1 except that the compositions of the cured products (composite materials) were changed as shown in table 3. On the obtained cured products (composite materials), in the same manner as in Example 1, (1) the visual evaluation of colored light, (2) the measurement of the wavelength of the colored light, (3) the evaluation of color tone compatibility with a colorimeter, (4) the visual evaluation of color tone compatibility and (5) the evaluation of the radial distribution function of inorganic spherical particles were performed. The results of the evaluations are shown in tables 3 to 5. Radial distribution function graphs for the cured products (composite materials) of Examples 2 to 4 are shown in FIGS. 4 to 6. In Examples 2 to 4, uniform compositions which satisfied conditions 1 and 2 of the radial distribution function were obtained at a ratio of 10 out of 10 tests with high reducibility.

Comparative Examples 1, 3 to 5

Cured products (composite materials) were obtained in the same manner as in Example 1 except that the compositions of the cured products (composite materials) were changed as shown in table 3. On the obtained cured products (composite materials), in the same manner as in Example 1, (1) the visual evaluation of colored light, (2) the measurement of the wavelength of the colored light, (3) the evaluation of color tone compatibility with a colorimeter and (4) the visual evaluation of color tone compatibility were performed. The composition (in the matrix column, the polymerizable monomer mixture providing the resin for forming the matrix is described) of the cured product (composite material) and the results of the evaluations are shown in tables 3 to 5.

Comparative Example 2

Figure 7:
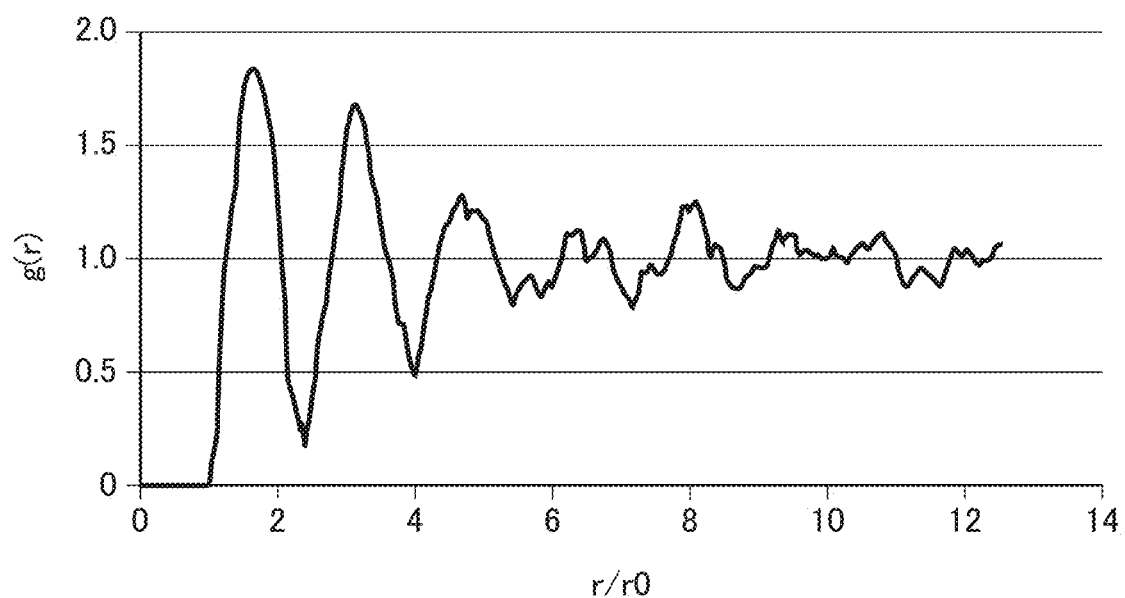
FIG. 7 is a diagram showing a radial distribution function graph for the composite material of Comparative Example 2.

0.3 parts by mass of CQ, 1.0 part by mass of DMBE and 0.15 parts by mass of HQME were added to 100 parts by mass of the polymerizable monomer mixture M1, they were mixed together and thus a uniform polymerizable monomer composition was prepared. Then, 400 parts by mass of G-PID2 and 0.5 parts by mass of the superfine particle group (G-SFP) were weighed, the polymerizable monomer composition described above was gradually added under red light and they were kneaded with a mortar so as to form a curable paste. Furthermore, the paste was defoamed under reduced pressure, and thus air bubbles were removed, with the result that a curable composition was produced. On the cured product (composite material) of the obtained curable composition, in the same manner as in Example 1, (1) the visual evaluation of colored light, (2) the measurement of the wavelength of the colored light, (3) the evaluation of color tone compatibility with a colorimeter, (4) the visual evaluation of color tone compatibility and (5) the evaluation of the radial distribution function of inorganic spherical particles were performed. The composition (in the matrix column, the polymerizable monomer mixture providing the resin for forming the matrix is described) of the cured product (composite material) and the results of the evaluations are shown in tables 3 to 5. A radial distribution function graph in the cured product (composite material) of Comparative Example 2 is shown in FIG. 7. In Comparative Example 2, with a ratio of one out of five tests, a satisfactory evaluation was not obtained. The evaluation results shown in the tables are based on this system.

As is understood from the results of Examples 1 to 4, it is found that when the conditions defined in the present invention are satisfied, the cured curable composition provides colored light in a black background and color tone compatibility is satisfactory.

As is understood from the results shown in FIGS. 2A, 2B and 3, in the cured product (composite material) obtained in Example 1, it was confirmed that in the position ($r_1/r_0$ was 1.03) where the closest particle-to-particle distance $r_1$ was 1.03 times the particle diameter $r_0$, the first local maximum peak of the radial distribution function g(r) was observed and the local minimum value of the radial distribution function g(r) between the closest particle-to-particle distance $r_1$ and the second closest particle-to-particle distance $r_2$ was 0.60, and it was confirmed that the cured product (composite material) obtained in Example 1 had the short-range order structure in the present invention.

As is understood from the results shown in FIG. 4, in the cured product (composite material) obtained in Example 2, it was confirmed that in a position ($r_1/r_0$ was 1.24) where the closest particle-to-particle distance $r_1$ was 1.24 times the particle diameter $r_0$, the first local maximum peak of the radial distribution function g(r) was observed and the local minimum value of the radial distribution function g(r) between the closest particle-to-particle distance $r_1$ and the second closest particle-to-particle distance $r_2$ was 0.62, and it was confirmed that the cured product (composite material) obtained in Example 2 had the short-range order structure in the present invention.

As is understood from the results shown in FIG. 5, in the cured product (composite material) obtained in Example 3, it was confirmed that in a position ($r_1/r_0$ was 1.41) where the closest particle-to-particle distance $r_1$ was 1.41 times the particle diameter $r_0$, the first local maximum peak of the radial distribution function g(r) was observed and the local minimum value of the radial distribution function g(r) between the closest particle-to-particle distance $r_1$ and the second closest particle-to-particle distance $r_2$ was 0.88, and it was confirmed that the cured product (composite material) obtained in Example 3 had the short-range order structure in the present invention.

As is understood from the results shown in FIG. 6, in the cured product (composite material) obtained in Example 4, it was confirmed that in a position ($r_1/r_0$ was 1.04) where the closest particle-to-particle distance $r_1$ was 1.04 times the particle diameter $r_0$, the first local maximum peak of the radial distribution function g(r) was observed and the local minimum value of the radial distribution function g(r) between the closest particle-to-particle distance $r_1$ and the second closest particle-to-particle distance $r_2$ was 0.80, and it was confirmed that the cured product (composite material) obtained in Example 4 had the short-range order structure in the present invention.

As is understood from the results of Comparative Examples 1 and 3 to 5, it is found that when the conditions defined in the present invention are not satisfied, a desired color tone is not obtained after curing and polishing (Comparative Example 1: $n_{(MX)} < n_{(G\text{-}PIDm)}$ is not satisfied), colored light is not provided in a black background (Comparative Example 3: the average primary particle diameter of G-PID was 80 nm, Comparative Example 4: the shape of the filler was irregular, Comparative Example 5: the average primary particle diameters of individual particles of G-PID$_m$ were less than 25 nm respectively) and color tone compatibility is poor.

As is understood from the results of Comparative Example 2, it is found that when the kneaded state of the composition is non-uniform, the conditions of the arrangement structure of the inorganic spherical particles defined in the present invention are not satisfied, and thus color tone compatibility with the tooth substance is poor.

As is understood from the results shown in FIG. 7, in the cured product (composite material) obtained in Comparative Example 2, it was confirmed that in a position ($r_1/r_0$ was 1.58) where the closest particle-to-particle distance $r_1$ was 1.58 times the particle diameter $r_0$, the first local maximum peak of the radial distribution function g(r) was observed and the local minimum value of the radial distribution function g(r) between the closest particle-to-particle distance $r_1$ and the second closest particle-to-particle distance $r_2$ was 0.18, and it was confirmed that the cured product (composite material) obtained in Comparative Example 2 did not have the short-range order structure in the present invention.

The invention claimed is:

1. A composite material comprising: a resin matrix and inorganic particles dispersed in the resin matrix,
the inorganic particles including:
an identical particle diameter spherical particle group (G-PID) which is formed with an aggregate of inorganic spherical particles having a predetermined average primary particle diameter within a range of 100 to 1000 nm and in which in a number-based particle size distribution of the aggregate, 90% or more of all the particles are present within a range of plus or minus 5% of the predetermined average primary particle diameter; and
a superfine particle group (G-SFP) that is formed with inorganic particles whose average primary particle diameter is less than 100 nm,
a number of the identical particle diameter spherical particle groups included in the inorganic particles is one or more,
when the number of the identical particle diameter spherical particle groups included in the inorganic particles is assumed to be a, and each of the identical particle diameter spherical particle groups are represented as G-PID$_m$ (where when a is 1, m is 1 whereas when a is equal to or greater than 2, m is a natural number from 1 to a) respectively in ascending order of the average primary particle diameters thereof, the average primary particle diameters of each G-PID$_m$ differ from each other by 25 nm or more,
the average primary particle diameter of the superfine particle group is smaller than the average primary particle diameter of G-PID$_1$ by 25 nm or more,
when a refractive index of the resin matrix at 25° C. is assumed to be $n_{(MX)}$, and a refractive index of the inorganic spherical particles of each G-PIDm at 25° C. is assumed to be $n_{(G\text{-}PIDm)}$, for any $n_{(G\text{-}PIDm)}$, a relationship of $n_{(MX)} < n_{(G\text{-}PIDm)}$ holds true and
an arrangement structure of the inorganic spherical particles of all the identical particle diameter spherical particle groups in the resin matrix has a short-range order structure which satisfies conditions 1 and 2 below:
[Condition 1] when a dimensionless number ($r/r_0$) which is standardized by dividing a distance r from a center of an arbitrary one of the inorganic spherical particles dispersed in the composite material by an average particle diameter $r_0$ of all the inorganic spherical particles dispersed in the composite material is assumed to be an x-axis, and a radial distribution function g(r) indicating a probability that another inorganic spherical particle is present at a point the distance r away from the center of the arbitrary inorganic spherical particle is assumed to be a y-axis, in a radial distribution function graph indicating a relationship of $r/r_0$ and g(r) which corresponds to r at that time, a closest particle-to-particle distance $r_1$ which is defined as r corresponding to a peak top of a peak closest to an origin among peaks appearing in the radial distribution function graph is a value that is 1 to 2 times the average particle diameter $r_0$ of all the inorganic spherical particles dispersed in the composite material;
[Condition 2] when r corresponding to a peak top of a peak second closest to the origin among the peaks appearing in the radial distribution function graph is assumed to be a second closest particle-to-particle distance $r_2$, a local minimum value of the radial distribution function g(r) between the closest particle-to-particle distance $r_1$ and the second closest particle-to-particle distance $r_2$ is a value of 0.56 to 1.10.

2. The composite material according to claim 1, wherein, based on an average particle density $\langle \rho \rangle$ of the inorganic spherical particles within an observation plane, a number do of the inorganic spherical particles which are present in a region between a circle of a distance r from an arbitrary inorganic spherical particle within the observation plane and a circle of a distance r+dr and an area da of the region (where da=2πr·dr) that are determined based on a scanning electron microscope image in which a plane within the composite material is assumed to be the observation plane, the radial distribution function g(r) is calculated by formula (1) below:

$$g(r)=\{1/<\rho>\}\times\{dn/da\} \quad (1).$$

3. The composite material according to claim 1, wherein a total content of the identical particle diameter spherical particle group with respect to 100 parts by mass of the resin matrix is 10 to 1500 parts by mass, and a content of the superfine particle group with respect to 100 parts by mass of the resin matrix is 0.1 to 50 parts by mass.

4. The composite material according to claim 1, wherein the average primary particle diameter of all the identical particle diameter spherical particle groups included in the inorganic particles falls within a range of 230 to 1000 nm, and the average primary particle diameter of the superfine particle group falls within a range of 3 to 75 nm.

5. The composite material according to claim 1, wherein Δn, defined as a difference $(n_{(g-PIDm)} - n_{(MX)})$ between $n_{(MX)}$ and $n_{(G-PIDm)}$, is 0.001 to 0.1 for any $n_{(G-PIDm)}$.

6. A dental filling restorative material which is formed of the composite material according to claim 1.

7. A curable composition for producing the composite material according to claim 1, the curable composition comprising:
a polymerizable monomer; inorganic particles; and a polymerization initiator,
wherein the inorganic particles include:
an identical particle diameter spherical particle group (G-PID) which is formed with an aggregate of inorganic spherical particles having a predetermined average primary particle diameter within a range of 100 to 1000 nm and in which in a number-based particle size distribution of the aggregate, 90% or more of all the particles are present within a range of plus or minus 5% of the predetermined average primary particle diameter; and
a superfine particle group (G-SFP) that is formed with inorganic particles whose average primary particle diameter is less than 100 nm,
a number of the identical particle diameter spherical particle groups included in the inorganic particles is one or more,
when the number of the identical particle diameter spherical particle groups included in the inorganic particles is assumed to be a, and each of the identical particle diameter spherical particle groups are represented as G-PID$_m$ (where when a is 1, m is 1 whereas when a is equal to or greater than 2, m is a natural number from 1 to a) respectively in ascending order of the average primary particle diameters thereof, the average primary particle diameters of each G-PID$_m$ differ from each other by 25 nm or more,
the average primary particle diameter of the superfine particle group is smaller than the average primary particle diameter of G-PID$_1$ by 25 nm or more and
when a refractive index of a cured product of the polymerizable monomer at 25° C. is assumed to be $n_{(MX)}$, and a refractive index of the inorganic spherical particles of each G-PID$_m$ at 25° C. is assumed to be $n_{(G-PIDm)}$, for any $n_{(G-PIDm)}$, a relationship of $n_{(MX)} < n_{(G-PIDm)}$ holds true.

8. The curable composition according to claim 7, wherein at least part of the one or more identical particle diameter spherical particle groups include one type of the identical particle diameter spherical particle group and a resin whose refractive index at 25° C. is less than a refractive index of the inorganic spherical particles of the one type of the identical particle diameter spherical particle group at 25° C., and are included as an organic-inorganic composite filler which does not include an identical particle diameter spherical particle group other than the one type of the identical particle diameter spherical particle group.

9. A method for producing a curable composition which includes a polymerizable monomer, inorganic particles that satisfy conditions (i) to (iv) below, and a polymerization initiator and which provides a cured product that produces a structural color of a predetermined color tone, the method comprising:
a mixing step of mixing the polymerizable monomer, the inorganic particles and the polymerization initiator,
wherein in the mixing step, mixing conditions are adopted in which it is confirmed, for a mixture obtained in the step, that a dispersed state of the inorganic particles in the cured product obtained by curing the mixture satisfies conditions (I) and (II) below, and the mixing is performed:
[Conditions which need to be satisfied by inorganic particles]
(i) the inorganic particles include an identical particle diameter spherical particle group (G-PID) which is formed with an aggregate of inorganic spherical particles having a predetermined average primary particle diameter within a range of 100 to 1000 nm and in which in a number-based particle size distribution of the aggregate, 90% or more of all the particles are present within a range of plus or minus 5% of the predetermined average primary particle diameter, and a number of the identical particle diameter spherical particle groups is one or more;
(ii) when the number of the identical particle diameter spherical particle groups included in the inorganic particles is assumed to be a, and each of the identical particle diameter spherical particle groups are represented as G-PID$_m$ (where when a is 1, m is 1 whereas when a is equal to or greater than 2, m is a natural number from 1 to a) respectively in ascending order of the average primary particle diameters thereof, the average primary particle diameters of each G-PID$_m$, differ from each other by 25 nm or more;
(iii) when a refractive index of a cured product of the polymerizable monomer at 25° C. is assumed to be $n_{(MX)}$, and a refractive index of the inorganic spherical particles of each G-PID$_m$, at 25° C. is assumed to be $n_{(G-PIDm)}$, for any $n_{(G-PIDm)}$, a relationship of $n_{(MX)} < n_{(G-PIDm)}$ holds true;
(iv) the inorganic particles include a superfine particle group (G-SFP) that is formed with inorganic particles whose average primary particle diameter is less than 100 nm and is smaller than the average primary particle diameter of G-PID$_1$ by 25 nm or more;
[Conditions which need to be satisfied by dispersed state]
(I) when a dimensionless number (r/r$_0$) which is standardized by dividing a distance r from a center of an arbitrary one of the inorganic spherical particles dispersed in the cured product of the mixture by an average particle diameter r$_0$ of all the inorganic spherical particles dispersed in the cured product of the mixture is assumed to be an x-axis, and a radial distribution function g(r) indicating a probability that another inorganic spherical particle is present at a point the distance r away from the center of the arbitrary inorganic spherical particle is assumed to be a y-axis, in a radial distribution function graph indicating a relationship of $r/r_0$ and g(r) which corresponds to r at that time, a closest particle-to-particle distance $r_1$ which is defined as r corresponding to a peak top of a peak closest to an origin among peaks appearing in the radial distribution function graph is a value that is 1 to 2 times the average particle diameter $r_0$ of all the inorganic spherical particles dispersed in the cured product of the mixture;

(II) when r corresponding to a peak top of a peak second closest to the origin among the peaks appearing in the radial distribution function graph is assumed to be a second closest particle-to-particle distance $r_2$, a local minimum value of the radial distribution function g(r) between the closest particle-to-particle distance $r_1$ and the second closest particle-to-particle distance $r_2$ is a value of 0.56 to 1.10.

10. The method for producing a curable composition according to claim 9, wherein, based on an average particle density <p> of the inorganic spherical particles within the observation plane, a number do of the inorganic spherical particles which are present in a region between a circle of a distance r from an arbitrary inorganic spherical particle within the observation plane and a circle of a distance r+dr and an area da of the region (where da=2πr·dr) that are determined based on a scanning electron microscope image in which a plane within the cured product of the mixture is assumed to be the observation plane, the radial distribution function g(r) is calculated by formula (1) below:

$$g(r) = \{1/<\rho>\} \times \{dn/da\} \qquad (1).$$

11. The method for producing a curable composition according to claim 9, wherein a method for determining the mixing conditions adopted in the mixing step is a method of (a) or (b) below:

(a) the method in which, previously, on a curable composition having a same or substantially same composition as the actually produced curable composition, a plurality of the mixing conditions are changed and the mixing is performed, the radial distribution function g(r) in the cured product of the mixture obtained when the mixing is performed under each of the mixing conditions is checked so as to determine the mixing conditions which satisfy the conditions (I) and (II) and the same mixing conditions as the determined mixing conditions are adopted;

(b) the method in which part of the mixture obtained partway through and/or after completion of the mixing step is sampled, whether or not a dispersed state of the inorganic particles in a cured product of the sampled mixture satisfies the conditions (I) and (II) is checked and the mixing is continued until these conditions are satisfied.

* * * * *